(12) United States Patent
Hong et al.

(10) Patent No.: US 11,583,008 B2
(45) Date of Patent: Feb. 21, 2023

(54) FINE PARTICLE GENERATING DEVICE

(71) Applicant: KT&G CORPORATION, Daejeon (KR)

(72) Inventors: Choong Sheek Hong, Yongin-si (KR); Seung Kiu Jeong, Gimhae-si (KR); Jung Ho Han, Daejeon (KR); Jong Sub Lee, Seongnam-si (KR); Hun Il Lim, Seoul (KR)

(73) Assignee: KT&G CORPORATION, Daejeon (KR)

( * ) Notice: Subject to any disclaimer, the term of this patent is extended or adjusted under 35 U.S.C. 154(b) by 702 days.

(21) Appl. No.: 16/479,114

(22) PCT Filed: Jan. 18, 2018

(86) PCT No.: PCT/KR2018/000870
§ 371 (c)(1),
(2) Date: Jul. 18, 2019

(87) PCT Pub. No.: WO2018/135887
PCT Pub. Date: Jul. 26, 2018

(65) Prior Publication Data
US 2019/0380389 A1     Dec. 19, 2019

(30) Foreign Application Priority Data

Jan. 18, 2017 (KR) .......... 10-2017-0008900
Jan. 18, 2017 (KR) .......... 10-2017-0008902
(Continued)

(51) Int. Cl.
*A24F 40/57* (2020.01)
*A24D 1/02* (2006.01)
(Continued)

(52) U.S. Cl.
CPC .......... *A24F 40/57* (2020.01); *A24D 1/02* (2013.01); *A24F 40/65* (2020.01); *A24F 40/20* (2020.01);
(Continued)

(58) Field of Classification Search
CPC .......... A24D 1/02; A61M 2205/3334; A61M 2205/3331; A61M 2205/3368;
(Continued)

(56) References Cited

U.S. PATENT DOCUMENTS

| | | |
|---|---|---|
| 5,388,594 A | 2/1995 | Counts et al. |
| 6,615,840 B1 | 9/2003 | Fournier et al. |

(Continued)

FOREIGN PATENT DOCUMENTS

| | | |
|---|---|---|
| CN | 103720056 A | 4/2014 |
| CN | 103974638 A | 8/2014 |

(Continued)

OTHER PUBLICATIONS

Communication dated Jan. 19, 2021, from the Japanese Patent Office in application No. 2019-559252.
(Continued)

*Primary Examiner* — Dana Ross
*Assistant Examiner* — Joe E Mills, Jr.
(74) *Attorney, Agent, or Firm* — Sughrue Mion, PLLC

(57) ABSTRACT

Provided is a fine particle generating apparatus outputting usage information, and in particular, a fine particle generating apparatus that generates fine particles through electrical heating and outputs usage information thereof to a user. Also, provided is a fine particle generating apparatus that generates fine particles by determining whether a puff has occurred according to a temperature variation amount per unit time. Also, provided is a fine particle generating apparatus or an aerosol generating apparatus capable of changing
(Continued)

puff conditions by controlling a heater. Also, provided is a fine particle generating apparatus that generates fine particles through electrical heating.

16 Claims, 13 Drawing Sheets

(30) Foreign Application Priority Data

| Jan. 18, 2017 | (KR) | 10-2017-0008903 |
|---|---|---|
| May 11, 2017 | (KR) | 10-2017-0058771 |
| May 11, 2017 | (KR) | 10-2017-0058773 |
| May 11, 2017 | (KR) | 10-2017-0058774 |
| Jan. 18, 2018 | (KR) | 10-2018-0006555 |
| Jan. 18, 2018 | (KR) | 10-2018-0006557 |
| Jan. 18, 2018 | (KR) | 10-2018-0006558 |

(51) Int. Cl.
```
A24F 40/65      (2020.01)
A61M 15/06      (2006.01)
G01K 7/16       (2006.01)
H05B 3/20       (2006.01)
A24F 40/20      (2020.01)
A24F 40/60      (2020.01)
A24F 40/95      (2020.01)
```

(52) U.S. Cl.
CPC .............. *A24F 40/60* (2020.01); *A24F 40/95* (2020.01); *A61M 15/06* (2013.01); *G01K 7/16* (2013.01); *H05B 3/20* (2013.01)

(58) Field of Classification Search
CPC ......... A61M 15/06; A24F 40/20; A24F 40/57; A24F 40/60; A24F 40/65; A24F 40/95; G01K 7/16; H05B 3/20
See application file for complete search history.

(56) References Cited

U.S. PATENT DOCUMENTS

| 9,067,029 | B2 | 6/2015 | Yamada et al. |
|---|---|---|---|
| 9,498,000 | B2 | 11/2016 | Kuczaj |
| 9,532,600 | B2 | 1/2017 | Thorens et al. |
| 9,693,587 | B2 | 7/2017 | Plojoux et al. |
| 10,028,533 | B2 | 7/2018 | Fursa et al. |
| 10,130,780 | B2 | 11/2018 | Talon |
| 10,143,232 | B2 | 12/2018 | Talon |
| 10,247,443 | B2 | 4/2019 | Flick |
| 10,333,330 | B2 | 6/2019 | Holzherr |
| 2013/0340750 | A1 | 12/2013 | Thorens et al. |
| 2014/0338680 | A1 | 11/2014 | Abramov et al. |
| 2015/0230521 | A1* | 8/2015 | Talon ............ A24F 40/50 131/328 |
| 2016/0157524 | A1* | 6/2016 | Bowen ............ A24F 40/57 702/50 |
| 2016/0360794 | A1 | 12/2016 | Li et al. |

FOREIGN PATENT DOCUMENTS

| EP | 2 915 443 A1 | 9/2015 |
|---|---|---|
| JP | 2010-506594 A | 3/2010 |
| JP | 2013-545474 A | 12/2013 |
| JP | 2014-533513 A | 12/2014 |
| JP | 2014-534814 A | 12/2014 |
| JP | 2015503916 A | 2/2015 |
| JP | 2015507477 A | 3/2015 |
| JP | 2015-524260 A | 8/2015 |
| JP | 2016524777 A | 8/2016 |
| KR | 10-2009-0023742 A | 3/2009 |
| KR | 10-1001077 A | 12/2010 |
| KR | 20-0455423 A | 9/2011 |
| KR | 10-2016-0147253 A | 12/2016 |
| WO | 2008/015918 A1 | 2/2008 |
| WO | 2013098398 A2 | 7/2013 |
| WO | 2016/091658 A1 | 6/2016 |
| WO | 2016/166064 A1 | 10/2016 |

OTHER PUBLICATIONS

Communication dated Nov. 27, 2020, from the European Patent Office in application No. 18742261.3.
Office Action dated May 9, 2020 from the Korean Intellectual Property Office in KR Application No. 10-2018-0006557.
Office Action dated May 12, 2020 from the Korean Intellectual Property Office in KR Application No. 10-2018-0006558.
Office Action dated Jun. 9, 2020 from the Korean Intellectual Property Office in KR Application No. 10-2018-0006555.
Communication dated Apr. 6, 2021 by the China National Intellectual Property Administration in application No. 201880007252.3.
International Search Report for PCT/KR2018/000870, dated May 29, 2018.
Office Action dated Aug. 2, 2022 in Japanese Application No. 2021-107338.
Office Action dated Aug. 2, 2022 in Japanese Application No. 2021-107339.
Extended Search Report dated Dec. 5, 2022 from the European Patent Office in EP Application No. 22189184.9.
Extended Search Report dated Dec. 5, 2022 from the European Patent Office in EP Application No. 22189195.5.

* cited by examiner

FINE PARTICLE GENERATING DEVICE

CROSS REFERENCE TO RELATED APPLICATIONS

This application is a National Stage of International Application No. PCT/KR2018/000870 filed Jan. 18, 2018, claiming priorities based on Korean Patent Application Nos. 10-2017-0008900 filed Jan. 18, 2017, 10-2017-0008902 filed Jan. 18, 2017, 10-2017-0008903 filed Jan. 18, 2017, 10-2017-0058771 filed May 11, 2017, 10-2017-0058773 filed May 11, 2017, 10-2017-0058774 filed May 11, 2017, 10-2018-0006555 filed Jan. 18, 2018, 10-2018-0006557 filed Jan. 18, 2018 and 10-2018-0006558 filed Jan. 18, 2018.

TECHNICAL FIELD

One or more embodiments relate to a fine particle generating apparatus or an aerosol generating apparatus capable of outputting usage information, and in particular, a fine particle generating apparatus or an aerosol generating apparatus that generates fine particles or aerosol through electrical heating, the fine particle generating apparatus or the aerosol generating apparatus determining whether there a puff occurs or outputting usage information of the generating apparatus.

One or more embodiments relate to a fine particle generating apparatus or an aerosol generating apparatus capable of adjusting puff conditions, and in particular, a fine particle generating apparatus or an aerosol generating apparatus that generates fine particles or aerosol through electrical heating, the fine particle generating apparatus or the aerosol generating apparatus capable of changing puff conditions by controlling a heater.

One or more embodiments relate to a fine particle generating apparatus of a heating type, and in particular, a fine particle generating apparatus generating fine particles through electrical heating.

BACKGROUND ART

Puff of a favored material, e.g., smoking, may be achieved by inhaling fine particles in the air, that is, aerosol. A tobacco of a cigarette type has been only unit for inhaling favored material, but recently, an electronic tobacco has been established as one of units for inhaling the favored material. An electronic tobacco is totally different from the cigarette type tobacco that generates smoke by burning an inhalation material in view of a smoking method, because the electronic tobacco generates fine particles by applying heat or ultrasonic waves to a cartridge, in which an inhalation material is contained in a liquid type, to vaporize the inhalation material. In addition, an electronic tobacco has advantages of hindering various harmful materials from being generated due to combustion.

Also, according to demand of consumers who prefer a general tobacco of the cigarette type, an electronic tobacco having a shape including a filter portion and a cigarette portion like a general tobacco has been suggested, and the electronic tobacco is configured so that a user may inhale the inhalation material through the filter portion that is equal to the general tobacco, wherein the inhalation material included in the cigarette portion is vaporized by using an electronic heater. In such above electronic tobacco, the cigarette portion is filled with paper that is impregnated or coated with the inhalation material, unlike in a general tobacco having the cigarette portion filled with dried tobacco leaves. When the electronic cigarette is inserted to a holder and a heater in the holder is heated to vaporize the inhalation material in the cigarette portion, the user may inhale the vaporized inhalation material through the filter portion. Since the vaporized inhalation material may be inhaled through the filter portion in the same mechanism as the traditional tobacco while having the advantage of not burning the tobacco like in the electronic tobacco according to the related art, the user may feel like smoking the traditional tobacco.

However, since the electronic tobacco according to the related art does not provide the user with usage information such as the number of times of using the tobacco, usage time period, etc., user convenience may degrade. Also, there may be a possibility that a minor or a third party uses the electronic tobacco in a state where the user who owns the electronic tobacco does not recognize it. In addition, when the air is introduced into the electronic tobacco, it may not be identified that the introduction is caused by puff of the user or a simple introduction of external air.

In addition, since the number of puffs, puff time, etc. are set in advance in the electronic tobacco according to the related art without regard to favor of the user, user convenience may degrade. Also, in the electronic tobacco according to the related art, the heater is operated at a set temperature without regard to the kind of vaporizing material, and thus, puff feeling suitable for the favor of the user may not be provided according to the kind of the vaporizing material.

Also, in the electronic tobacco according to the related art, as shown in FIG. 8, when the user pushes a button provided on the electronic tobacco to use the electronic tobacco, the electronic tobacco enters a pre-heating stage, in which a temperature rapidly increases to a changing point (t) of a time variation axis, the pre-heating stage ends at a changing point (c) of a temperature variation axis, and then, to a changing point (c+2), the temperature decreases between the changing point (t) and a changing point (t+1) and then slightly increases from the changing point (t+1) to a changing point (t+2) of the time variation axis with a slight inclination between the changing point (c+2) and the changing point (c+1) in the temperature variation axis while maintaining the vaporizing temperature. Then, the use of the electronic tobacco is terminated at the changing point (t+2) of the time variation axis, and then, the temperature rapidly decreases. In an operation of the electronic tobacco, an electric power supplied at starting of the electronic tobacco or during the pre-heating stage is very high, the electronic tobacco consumes a lot of power of the battery and generates excessive heat. Also, after the pre-heating stage, the battery operates maintaining a vaporizing temperature at a maximum output, from which consumed power is substituted, and thus, there is not a sufficient time for dissipating excessive heat that is generated and internal and external temperature of the housing of the electronic tobacco increase. Accordingly, the battery of the electronic tobacco is rapidly consumed.

DESCRIPTION OF EMBODIMENTS

Technical Problem

The present disclosure provides a fine particle generating apparatus capable of using various kinds of inhalation materials without being accompanied by combustion.

The present disclosure provides a fine particle generating apparatus capable of providing a user with usage information thereof in various viewpoints.

The present disclosure provides a method and apparatus for determining whether a puff occurs.

The present disclosure provides a fine particle generating apparatus, puff conditions of which may be freely changed by a user according to his/her preference.

The present disclosure provides a method and apparatus for controlling power supply to a heater by sensing the air applied according to a puff.

The present disclosure provides a fine particle generating apparatus capable of adjusting power supplied to the heater.

The present disclosure provides a fine particle generating apparatus including a heater of various shapes having excellent heat conduction efficiency.

Solution to Problem

The present disclosure provides a device for generating fine particles through electrical heating.

Advantageous Effects of Disclosure

According to one or more embodiments, a fine particle generating apparatus that does not need to combust is provided.

According to one or more embodiments, usage information of an apparatus may be displayed to a user.

According to one of more embodiments, using of the device may be restricted to various conditions.

According to one or more embodiments, whether a puff occurs may be determined according to a temperature variation amount per unit time.

According to one or more embodiments, a fine particle generating apparatus has puff conditions that may be changed by a user according to preference.

According to one or more embodiments, a vaporizing material may be heated with a suitable temperature profile to increase user's satisfaction when inhaling the vaporized material.

According to one or more embodiments, a temperature of the heater may be maintained at a predetermined level or greater even with puff.

According to one or more embodiments, the fine particle generating apparatus may be operated in a temperature control profile corresponding to the air applied through the puff.

According to one or more embodiments, a fine particle generating apparatus capable of effectively using electric power of a power storage device by adjusting power supplied to the heater may be provided.

According to one or more embodiments, a fine particle generating apparatus including a heater of various shapes having excellent heat conduction efficiency may be provided.

BEST MODE

Figure 1:
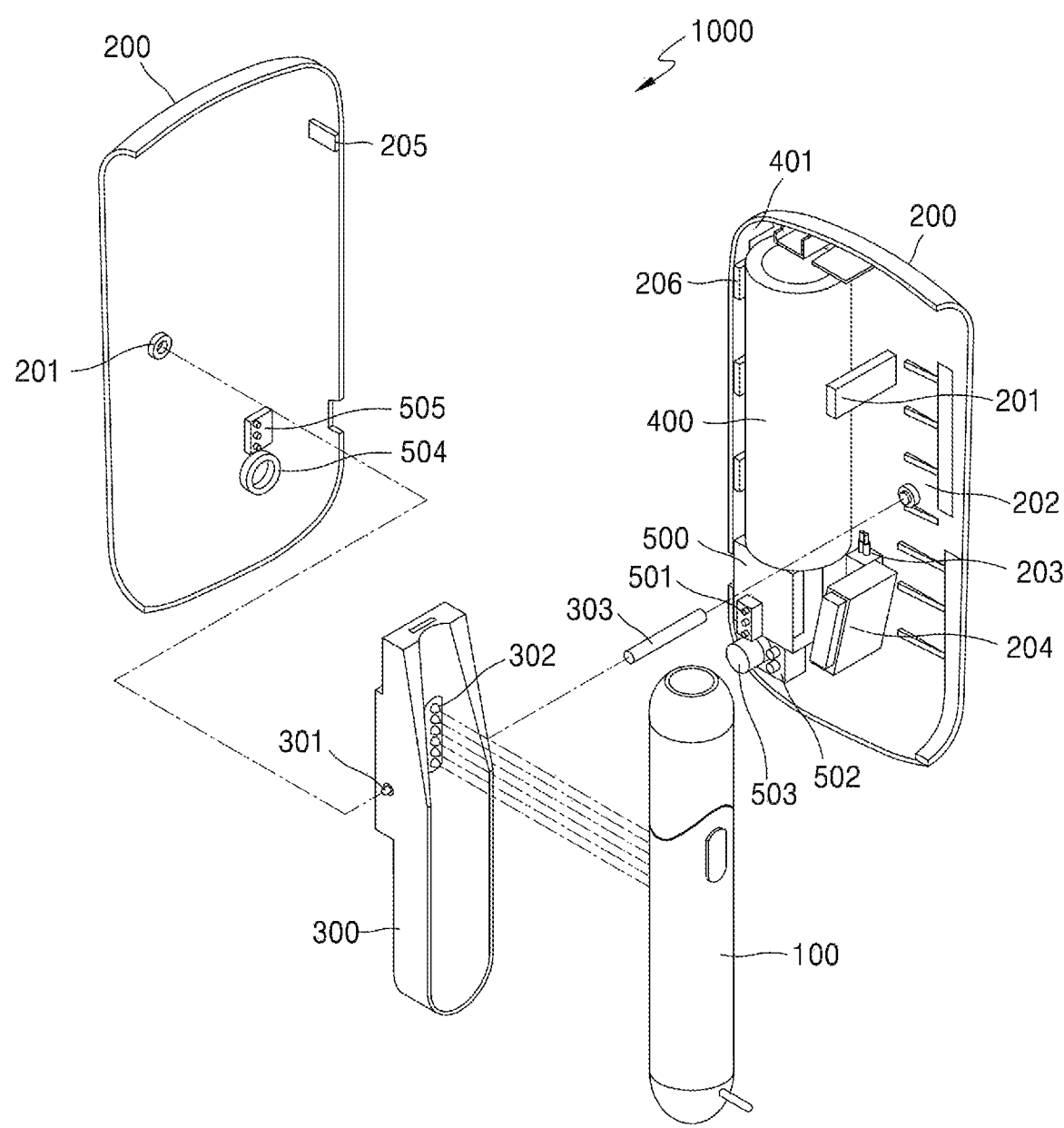
FIG. 1 is an exploded perspective view of a fine particle generating apparatus and an external power supply device according to an embodiment.

To achieve the above purpose, according to an aspect of the disclosure, a fine particle generating apparatus that generates fine particles so that a user may inhale the fine particles through a puff, the fine particle generating apparatus includes: a heater generating heat due to resistance when receiving electric current; a power storage device capable of instantly supplying high electric power to the heater; a display device displaying usage information of the fine particle generating apparatus to the user; and a control device controlling at least one of the above-stated elements, wherein the heater generates fine particles by heating a vaporizing material including a material (vaporizing material) that vaporizes when being heated to a predetermined temperature or greater.

According to an embodiment of the disclosure, usage information of a device displays the number of daily uses of the fine particle generating apparatus, and one time use may be defined by the number of puffs or a used time period.

According to an embodiment of the disclosure, the fine particle generating apparatus includes a temperature sensor for measuring a temperature of the heater.

According to an embodiment of the disclosure, the fine particle generating apparatus includes a calculation device that determines whether a puff of the user has occurred by sensing an instant temperature variation rate of the heater.

According to an embodiment of the disclosure, the fine particle generating apparatus increases the number of uses by one when the puff of the user occurs at least once within ten minutes after turning on the fine particle generating apparatus.

According to an embodiment of the disclosure, the fine particle generating apparatus includes a charger for charging a power storage device with external power.

According to an embodiment of the disclosure, the fine particle generating apparatus includes an information transmitter for transmitting usage information to outside.

According to an embodiment of the disclosure, the fine particle generating apparatus includes an external power supply device including: a power storage device for supply;

a power transmitter connected to the fine particle generating apparatus through wires or wirelessly to transmit power to the fine particle generating apparatus; a power display device for displaying remaining power of the power storage device for supply; a display device for displaying usage information of the fine particle generating apparatus; and a controller for controlling at least one of the above stated elements.

According to an embodiment of the disclosure, on being connected to the fine particle generating apparatus, the external power supply device synchronizes usage information with the fine particle generating apparatus through wires or wirelessly.

According to an embodiment of the disclosure, when the energy supplied to the fine particle generating apparatus is equal to or greater than a predetermined amount, in particular, energy consumed by at least one puff, the external power supply device increases the number of using the fine particle generating apparatus by one.

According to an embodiment of the disclosure, both the fine particle generating apparatus and the external power supply device or one of the fine particle generating apparatus and the external power supply device may include a timer.

According to an embodiment of the disclosure, both the fine particle generating apparatus and the external power supply device or one of the fine particle generating apparatus and the external power supply device may include an input unit for resetting the number of uses of the fine particle generating apparatus.

According to an embodiment of the disclosure, the number of daily uses is reset every day.

According to an embodiment of the disclosure, the fine particle generating apparatus may include an input unit that may set the maximum number of daily uses that is one piece of the usage information.

According to an embodiment of the disclosure, the fine particle generating apparatus blocks the supply of electric power to the fine particle generating apparatus after the maximum number of daily uses has reached.

According to an embodiment of the disclosure, the fine particle generating apparatus may be connected to a smart device through wires or wirelessly to synchronize the usage information.

According to an embodiment of the disclosure, the smart device connected to the fine particle generating apparatus through wires or wirelessly may analyze the usage information and display analyzing content.

According to an embodiment of the disclosure, the fine particle generating apparatus may include a biometric device and may be controlled only by a user who is authenticated by the biometric device.

According to an embodiment of the disclosure, the usage information of the fine particle generating apparatus may be corrected only by the user who is authenticated by the biometric device.

According to an embodiment of the disclosure, the fine particle generating apparatus may include an adult authentication device, and may be controlled only by a user who is authenticated as an adult by the adult authentication device.

According to an embodiment of the disclosure, the fine particle generating apparatus may include an inhalation sensor that senses an inhalation amount generated per one time puff of the user, and a nicotine calculator that calculates a nicotine puff amount that is one piece of the usage information, based on the sensed inhalation amount.

According to another embodiment of the disclosure, an aerosol generating apparatus includes a heater generating aerosol by electricity; a processor determining whether the puff has occurred according to a sensed temperature variation amount per unit time, and generating aerosol by supplying electric power to the heater when the puff has occurred; and a battery for supplying electric power to the heater and the processor.

Also, the processor determines that the puff has occurred when the temperature variation amount per unit time of the heater is equal to or greater than a preset value, and determines that the puff does not occur when the temperature variation amount per unit time of the heater is less than the preset value.

The aerosol generating apparatus further includes an inhalation sensor for sensing the air introduced to the aerosol generating apparatus; and a temperature sensor for determining the temperature variation amount per unit time of the heater. The processor obtains information indicating the temperature variation amount per unit time of the heater from the temperature sensor when the inhalation sensor senses the air introduced to the aerosol generating apparatus, and determines whether the puff has occurred according to the temperature variation amount per unit time of the heater.

When a velocity of air introduced into the aerosol generating apparatus is equal to or greater than a preset value, the temperature sensor senses a temperature variation amount per unit time of the heater.

Also, when a velocity of air introduced into the aerosol generating apparatus is equal to or greater than a preset value, the processor determines whether the section behavior has occurred according to a temperature variation amount per unit time of the heater.

Also, when the puff has occurred, the processor may update the stored number of uses and/or the number of puffs to be increased.

Also, the aerosol generating apparatus may further include a display for displaying the number of uses and/or the number of puffs.

According to another aspect of the disclosure, an aerosol generating method includes: sensing a temperature variation amount per unit time; determining whether a puff has occurred according to the temperature variation amount per unit time; and when the puff has occurred, generating aerosol by supplying electric power to a heater.

Also, the aerosol generating method may further include sensing the air introduced to the aerosol generating apparatus, and the sensing of the temperature variation amount per unit time may sense the temperature variation amount per unit time of the heater when the air introduced to the aerosol generating apparatus is sensed.

Also, the determining of whether the puff has occurred may include determining that the puff has occurred when the temperature variation amount per unit time of the heater is equal to or greater than a preset value, and determining that the puff does not occur when the temperature variation amount per unit time of the heater is less than the preset value.

Also, according to another aspect of the disclosure, a computer program having embodied thereon the above method stored in a recording medium is provided.

Also, the fine particle generating apparatus according to another aspect of the disclosure generates fine particles so that the fine particles are inhaled through a puff of a user, and the fine particle generating apparatus includes a heater generating heat due to resistance when receiving electric current, a power storage device capable of instantly supplying high electric power to the heater, a puff condition changing unit capable of changing the puff conditions of fine particles, and a control device controlling at least one of the above-stated elements, wherein the heater generates the fine particle generating apparatus by heating a vaporizing material including a material that is vaporized when being heated to a predetermined temperature or greater (vaporizing material).

Also, according to an embodiment of the disclosure, the fine particle generating apparatus may include an external power supply device connected to the fine particle generating apparatus to supply the electric power to the power storage device.

Also, according to an embodiment of the disclosure, the puff condition changing unit may change the puff condition in a manner of selecting one of at least two puff conditions.

Also, according to an embodiment of the disclosure, the puff condition changing unit includes an input device and changes the puff conditions by receiving a user input through the input device.

According to an embodiment of the disclosure, the puff conditions of the fine particles may at least include the temperature of the heater as an element.

Also, according to an embodiment of the disclosure, a vaporizing material including a plurality of vaporizing materials having different minimum vaporizing temperatures from one another may be used.

Also, according to an embodiment of the disclosure, at least some of the plurality of vaporizing materials include nicotine, and some may have different content in nicotine.

Also, according to an embodiment of the disclosure, the fine particle generating apparatus may include a control device that maintains the temperature of the heater, which is selected as the puff condition.

Also, according to an embodiment of the disclosure, the puff condition of the fine particles may include an inhalation amount generated per puff of the user as an element.

Also, according to an embodiment of the disclosure, the fine particle generating apparatus may include an inhalation sensor that senses the inhalation amount per one puff of the user.

Also, according to an embodiment of the disclosure, the control device may predict the temperature of the heater, which descends due to the puff of the user, by sensing the inhalation amount, and controls the power supply so as to maintain the temperature of the heater constantly.

Also, according to an embodiment of the disclosure, the fine particle generating apparatus may include an RFID reader that may recognize an RFID tag that may be included in the vaporizing material.

Also, according to an embodiment of the disclosure, the control device may change a temperature control profile according to the vaporizing material that is recognized by the RFID reader.

Also, according to an embodiment of the disclosure, a vaporizing material including a vaporizing material that is not harmful to the human body may be used.

Also, according to an embodiment of the disclosure, a vaporizing material including a vaporizing material that is good for health of the human body may be used.

Also, according to an embodiment, a vaporizing material including a material causing pharmacological action with respect to the human body may be used.

Also, according to an embodiment of the disclosure, a vaporizing material including a material including phytoncide may be used.

Also, according to another aspect of the disclosure, an aerosol generating apparatus includes a sensor for sensing air applied to the aerosol generating apparatus according to a puff; a processor for controlling power supply to the heater according to a result of sensing the air applied to the aerosol generating apparatus; and the heater maintaining the temperature within a preset range according to a control of the processor.

Also, the result of sensing includes an inhalation amount generated per one puff of the user, and the processor may determine a predicted descending temperature of the heater according to the inhalation amount per one puff of the user and may control the power supply to the heater according to the predicted temperature so that the temperature of the heater may be maintained within a preset range.

Also, the processor may control the supply of electric power to the heater, and the electric power is supplied to the heater before the temperature of the heater decreases to a predetermined temperature or less due to the air applied to the aerosol generating apparatus.

Also, the sensor may sense at least one of an amount of the air applied to the aerosol generating apparatus according to the puff, a temperature of the air, and the velocity of the air, and the processor may control the power supply to the heater based on at least one of the amount of the air, the temperature of the air, and the velocity of the air.

Also, according to another aspect of the disclosure, an aerosol generating method includes: sensing air applied to an aerosol generating apparatus according to puff; controlling power supply to a heater according to a result of sensing the air applied to the aerosol generating apparatus; and maintaining a temperature of the heater within a preset range according to a control on the power supply to the heater.

Also, according to another aspect of the disclosure, an aerosol generating apparatus includes: a sensor for sensing air applied to the aerosol generating apparatus according to the puff; a processor for determining a temperature control profile of the heater according to a result of sensing the air applied to the aerosol generating apparatus, and controlling power supply to the heater according to the temperature control profile; and the heater for generating aerosol according to control of the processor.

Also, the processor may determine one temperature control profile corresponding to the sensing result from among a plurality of temperature control profiles.

Also, the sensing result includes an inhalation amount generated per one puff of the user, and the processor may determine a temperature control profile corresponding to the inhalation amount per one puff of the user from among the plurality of temperature control profiles.

Also, the sensor may sense at least one of an amount of the air applied to the aerosol generating apparatus according to the puff, a temperature of the air, and a velocity of the air, and the processor may determine one of a plurality of temperature control profiles based on at least one of the sensed amount of the air, the temperature of the air, and the velocity of the air.

Also, according to another aspect of the disclosure, an aerosol generating method includes: sensing air applied to an aerosol generating apparatus according to puff; determining a temperature control profile for a heater according to a result of sensing the air applied to the aerosol generating apparatus, and controlling power supply to the heater according to the temperature control profile; and the heater generating aerosol according to the control on the power supply to the heater.

Also, according to another aspect of the disclosure, a computer program stored in a recording medium for executing one of the methods according to above seventh to ninth aspects may be provided.

Also, another aspect the disclosure includes a heater; a battery supplying power to the heater; a memory storing one or more instructions for controlling the heater; and a processor operating the battery via the one or more instructions, wherein the one or more instructions include temperature profile information of the heater.

Also, according to an embodiment of the disclosure, the processor includes the memory.

Also, according to an embodiment of the disclosure, an input unit providing an input signal for starting the operation to the processor is further provided, and the processor receiving the input signal accesses the memory.

Also, according to an embodiment of the disclosure, the temperature profile information includes at least one vaporizing temperature retaining section for the heater, in which the vaporizing material is heated to a predetermined temperature or greater to discharge a vaporizing material, at least one vaporizing temperature decreasing section, at least one minimum vaporizing temperature retaining section, and at least one puff section.

Also, according to an embodiment of the disclosure, a temperature sensor for providing the processor with temperature measurement information generated by measuring temperature of the heater is further provided.

Also, according to an embodiment of the disclosure, the processor adjusts the power supplied by the battery by using a result of comparing the temperature measurement information with the temperature profile information.

Also, according to an embodiment of the disclosure, there are further provided a case, a holder located between the case and the heater for supporting a cigarette that penetrates through the heater via the case; and an insulating member located between the case and the holder.

Also, according to an embodiment of the disclosure, the insulating member may include an insulator for reducing thermal loss of the heater.

Also, according to an embodiment of the disclosure, a case and a holder supporting a cigarette penetrating the heater through the case between the case and the heater are further provided, and an insulating member is attached to a contact surface of the holder with the case.

Also, according to an embodiment of the disclosure, the insulating member may include an insulator for reducing thermal loss of the heater.

To achieve the purpose, a fine particle generating apparatus that generates fine particles so that the fine particles may be inhaled through a puff of the user includes: a heater generating heat due to resistance when receiving electric power; a power storage device capable of instantly supplying high electric power to the heater; and a control device for controlling the heater, wherein the heater generates fine particles by heating a vaporizing material including a material (vaporizing material) that vaporizes at a predetermined temperature or higher.

According to an embodiment of the disclosure, the control device controls the heater to be heated to a combustion temperature of the vaporizing material or less so that the vaporizing material is not burn.

According to an embodiment of the disclosure, the control device controls the heater to a pre-heating stage, a vaporizing temperature reaching stage, and a vaporizing temperature retaining stage.

According to an embodiment of the disclosure, the control device heats the heater to a temperature close to the combustion temperature of the vaporizing temperature under the combustion temperature in the pre-heating stage.

Also, according to an embodiment of the disclosure, the control device stops supplying of the electric power to the heater so that the temperature of the heater descends to the minimum vaporizing temperature of the vaporizing material in the vaporizing temperature reaching stage.

Also according to an embodiment of the disclosure, the control device controls the temperature of the heater to be maintained between the maximum vaporizing temperature, at which the vaporizing amount of the vaporizing material is the maximum, and the minimum vaporizing temperature.

Also, according to an embodiment of the disclosure, the control device supplies electric power to the heater when the temperature of the heater reaches the minimum vaporizing temperature, and stops supplying of electric power to the heater when the temperature of the heater reaches the maximum vaporizing temperature.

Also, according to an embodiment of the disclosure, the fine particle generating apparatus may include a calculation device that recognizes that a puff of the user has occurred when the temperature descending rate of the heater increases.

Also, according to an embodiment of the disclosure, when a puff of the user is recognized, the control device supplies electric power to the heater to the maximum to heat the heater to the maximum vaporizing temperature.

According to an embodiment of the disclosure, the fine particle generating apparatus includes a temperature sensor for measuring a temperature of the heater.

Also, according to an embodiment of the disclosure, the fine particle generating apparatus senses the temperature by sensing a variation in a thermal resistance of the heater.

Also, according to an embodiment of the disclosure, the fine particle generating apparatus includes a temperature sensor attached to the heater.

Also, according to an embodiment of the disclosure, the heater has a sewing needle shape.

Also, according to an embodiment of the disclosure, the heater has a pentagonal plane shape.

Also, according to an embodiment of the disclosure, the heater has a cylindrical shape with a hollow therein.

Also, according to an embodiment of the disclosure, the heater has a cylindrical shape with a hollow therein, and the vaporizing material is inserted in the heater and heated.

MODE OF DISCLOSURE

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant. In this case, the meaning of the selected terms will be described in the detailed description. Thus, the terms used herein have to be defined based on the meaning of the terms together with the description throughout the specification.

It will be further understood that the terms "comprises" and/or "comprising," when used in this specification, specify the presence of stated components, but do not preclude the presence or addition of one or more components. In addition, the terms such as " . . . unit", "module", etc. provided herein indicates a unit performing at least one function or operation, and may be realized by hardware, software, or a combination of hardware and software.

Hereinafter, one or more embodiments of the present disclosure will be described in detail with reference to accompanying drawings to the extent that one of ordinary skill in the art would be able to carry out the present disclosure. However, the present disclosure may be implemented in various manners, and is not limited to one or more embodiments described herein.

According to an aspect of the disclosure, a fine particle generating apparatus that generates fine particles so that a user may inhale the fine particles through a puff, the fine particle generating apparatus includes: a heater generating heat due to resistance when receiving electric current; a power storage device capable of instantly supplying high electric power to the heater; a display device displaying usage information of the fine particle generating apparatus to the user; and a control device controlling at least one of the above-stated elements, wherein the heater generates fine particles by heating a vaporizing material including a material (vaporizing material) that vaporizes when being heated to a predetermined temperature or greater.

According to an embodiment of the disclosure, usage information of a device displays the number of daily uses of the fine particle generating apparatus, and one time use may be defined by the number of puffs or a used time period.

According to an embodiment of the disclosure, the fine particle generating apparatus includes a temperature sensor for measuring a temperature of the heater.

According to an embodiment of the disclosure, the fine particle generating apparatus includes a calculation device that determines whether a puff of the user has occurred by sensing an instant temperature variation rate of the heater.

According to an embodiment of the disclosure, the fine particle generating apparatus increases the number of uses by one when the puff of the user occurs at least once within ten minutes after turning on the fine particle generating apparatus.

According to an embodiment of the disclosure, the fine particle generating apparatus includes a charger for charging a power storage device with external power.

According to an embodiment of the disclosure, the fine particle generating apparatus includes an information transmitter for transmitting usage information to outside.

According to an embodiment of the disclosure, the fine particle generating apparatus includes an external power supply device including: a power storage device for supply; a power transmitter connected to the fine particle generating apparatus through wires or wirelessly to transmit power to the fine particle generating apparatus; a power display device for displaying remaining power of the power storage device for supply; a display device for displaying usage information of the fine particle generating apparatus; and a controller for controlling at least one of the above stated elements.

According to an embodiment of the disclosure, on being connected to the fine particle generating apparatus, the external power supply device synchronizes usage information with the fine particle generating apparatus through wires or wirelessly.

According to an embodiment of the disclosure, when the energy supplied to the fine particle generating apparatus is equal to or greater than a predetermined amount, in particular, energy consumed by at least one puff, the external power supply device increases the number of using the fine particle generating apparatus by one.

According to an embodiment of the disclosure, both the fine particle generating apparatus and the external power supply device or one of the fine particle generating apparatus and the external power supply device may include a timer.

According to an embodiment of the disclosure, both the fine particle generating apparatus and the external power supply device or one of the fine particle generating apparatus and the external power supply device may include an input unit for resetting the number of uses of the fine particle generating apparatus.

According to an embodiment of the disclosure, the number of daily uses is reset every day.

According to an embodiment of the disclosure, the fine particle generating apparatus may include an input unit that may set the maximum number of daily uses that is one piece of the usage information.

According to an embodiment of the disclosure, the fine particle generating apparatus blocks the supply of electric power to the fine particle generating apparatus after the maximum number of daily uses has reached.

According to an embodiment of the disclosure, the fine particle generating apparatus may be connected to a smart device through wires or wirelessly to synchronize the usage information.

According to an embodiment of the disclosure, the smart device connected to the fine particle generating apparatus through wires or wirelessly may analyze the usage information and display analyzing content.

According to an embodiment of the disclosure, the fine particle generating apparatus may include a biometric device and may be controlled only by a user who is authenticated by the biometric device.

According to an embodiment of the disclosure, the usage information of the fine particle generating apparatus may be corrected only by the user who is authenticated by the biometric device.

According to an embodiment of the disclosure, the fine particle generating apparatus may include an adult authentication device, and may be controlled only by a user who is authenticated as an adult by the adult authentication device.

According to an embodiment of the disclosure, the fine particle generating apparatus may include an inhalation sensor that senses an inhalation amount generated per one time puff of the user, and a nicotine calculator that calculates a nicotine inhalation amount that is one piece of the usage information, based on the sensed inhalation amount.

Also, the fine particle generating apparatus according to another aspect of the disclosure generates fine particles so that the fine particles are inhaled through a puff of a user, and the fine particle generating apparatus includes a heater generating heat due to resistance when receiving electric current, a power storage device capable of instantly supplying high electric power to the heater, a puff condition changing unit capable of changing the puff conditions of fine particles, and a control device controlling at least one of the above-stated elements, wherein the heater generates the fine particle generating apparatus by heating a vaporizing material including a material that is vaporized when being heated to a predetermined temperature or greater (vaporizing material).

Also, according to an embodiment of the disclosure, the fine particle generating apparatus may include an external power supply device connected to the fine particle generating apparatus to supply the electric power to the power storage device.

Also, according to an embodiment of the disclosure, the puff condition changing unit may change the puff condition in a manner of selecting one of at least two puff conditions.

Also, according to an embodiment of the disclosure, the puff condition changing unit includes an input device and changes the puff conditions by receiving a user input through the input device.

According to an embodiment of the disclosure, the puff conditions of the fine particles may at least include the temperature of the heater as an element.

Also, according to an embodiment of the disclosure, a vaporizing material including a plurality of vaporizing materials having different minimum vaporizing temperatures from one another may be used.

Also, according to an embodiment of the disclosure, at least some of the plurality of vaporizing materials include nicotine, and some may have different content in nicotine.

Also, according to an embodiment of the disclosure, the fine particle generating apparatus may include a control device that maintains the temperature of the heater, which is selected as the puff condition.

Also, according to an embodiment of the disclosure, the puff condition of the fine particles may include an inhalation amount generated per puff of the user as an element.

Also, according to an embodiment of the disclosure, the fine particle generating apparatus may include an inhalation sensor that senses the inhalation amount per one puff of the user.

Also, according to an embodiment of the disclosure, the control device may predict the temperature of the heater, which descends due to the puff of the user, by sensing the inhalation amount, and controls the power supply so as to maintain the temperature of the heater constantly.

Also, according to an embodiment of the disclosure, the fine particle generating apparatus may include an RFID reader that may recognize an RFID tag that may be included in the vaporizing material.

Also, according to an embodiment of the disclosure, the control device may change a temperature control profile according to the vaporizing material that is recognized by the RFID reader.

Also, according to an embodiment of the disclosure, a vaporizing material including a vaporizing material that is not harmful to the human body may be used.

Also, according to an embodiment of the disclosure, a vaporizing material including a vaporizing material that is good for health of the human body may be used.

Also, according to an embodiment, a vaporizing material including a material causing pharmacological action with respect to the human body may be used.

Also, according to an embodiment of the disclosure, a vaporizing material including a material including phytoncide may be used.

According to an aspect of the disclosure, a fine particle generating apparatus that generates fine particles so that a user may inhale the fine particles through a puff, the fine particle generating apparatus includes: a heater generating heat due to resistance when receiving electric current; a power storage device capable of instantly supplying high electric power to the heater; and a control device controlling the heater, wherein the heater generates fine particles by heating a vaporizing material including a material (vaporizing material) that vaporizes when being heated to a predetermined temperature or greater. In particular, the fine particles are fine enough to float in the air, that is, aerosol.

According to an embodiment of the disclosure, the control device controls the heater to be heated to a combustion temperature of the vaporizing material or less so that the vaporizing material is not burn. The vaporizing material may be in a liquid phase or a solid phase. The vaporizing material may include, for example, nicotine, or a material having a certain favor or flavor.

According to an embodiment of the disclosure, the control device controls the heater to a pre-heating stage, a vaporizing temperature reaching stage, and a vaporizing temperature retaining stage.

According to an embodiment of the disclosure, the control device heats the heater to a temperature close to the combustion temperature of the vaporizing temperature under the combustion temperature in the pre-heating stage.

Also, according to an embodiment of the disclosure, the control device stops supplying of the electric power to the heater so that the temperature of the heater descends to the minimum vaporizing temperature of the vaporizing material in the vaporizing temperature reaching stage.

Also according to an embodiment of the disclosure, the control device controls the temperature of the heater to be maintained between the maximum vaporizing temperature, at which the vaporizing amount of the vaporizing material is the maximum, and the minimum vaporizing temperature.

Also, according to an embodiment of the disclosure, the control device supplies electric power to the heater when the temperature of the heater reaches the minimum vaporizing temperature, and stops supplying of electric power to the heater when the temperature of the heater reaches the maximum vaporizing temperature.

Also, according to an embodiment of the disclosure, the fine particle generating apparatus may include a calculation device that recognizes that a puff of the user has occurred when the temperature descending rate of the heater increases.

Also, according to an embodiment of the disclosure, when a puff of the user is recognized, the control device supplies electric power to the heater to the maximum to heat the heater to the maximum vaporizing temperature.

According to an embodiment of the disclosure, the fine particle generating apparatus includes a temperature sensor for measuring a temperature of the heater.

Also, according to an embodiment of the disclosure, the fine particle generating apparatus senses the temperature by sensing a variation in a thermal resistance of the heater.

Also, according to an embodiment of the disclosure, the fine particle generating apparatus includes a temperature sensor attached to the heater.

Also, according to an embodiment of the disclosure, the heater has a sewing needle shape.

Also, according to an embodiment of the disclosure, the heater has a pentagonal plane shape.

Also, according to an embodiment of the disclosure, the heater has a cylindrical shape with a hollow therein.

Also, according to an embodiment of the disclosure, the heater has a cylindrical shape with a hollow therein, and the vaporizing material is inserted in the heater and heated.

Hereinafter, one or more embodiments of the disclosure will be described in detail with reference to the accompanying drawings. Also, aerosol may denote air including fine particles, and hereinafter, a fine particle generating apparatus may denote a device for generating aerosol. For convenience of description, fine particles may be a concept including aerosol. Therefore, generation of fine particles may denote generation of aerosol including fine particles.

Figure 2:
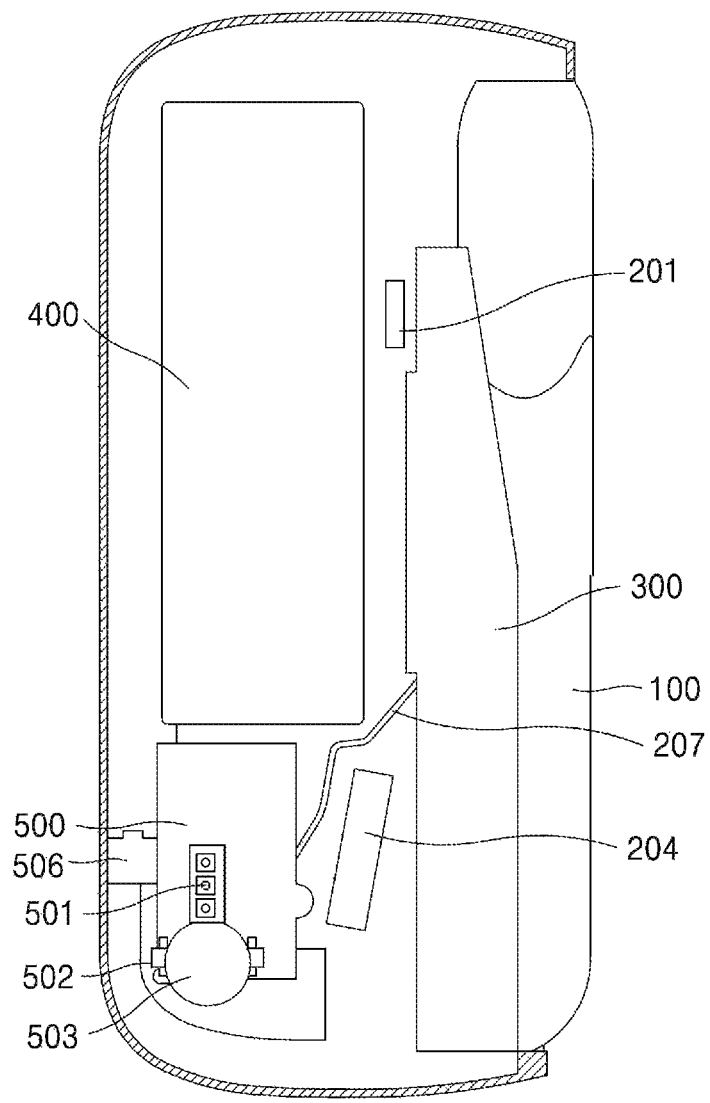
FIG. 2 is a cross-sectional view of a fine particle generating apparatus and an external power supply device according to an embodiment.
Figure 3:
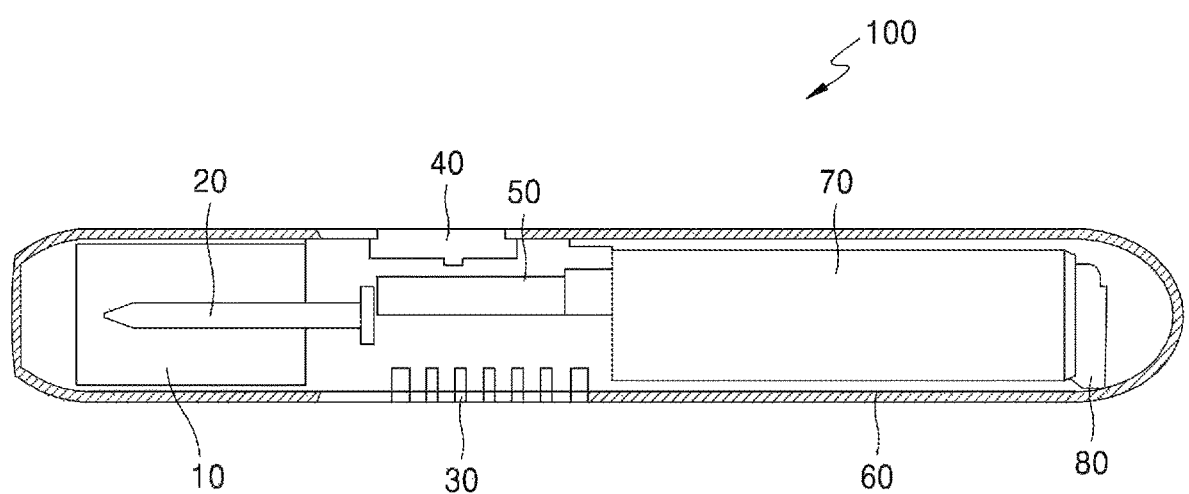
FIG. 3 is a cross-sectional view of a fine particle generating apparatus according to an embodiment.

FIG. 1 is an exploded perspective view of a fine particle generating apparatus and an external power supply device according to an embodiment, FIG. 2 is a cross-sectional view of the fine particle generating apparatus and the external power supply device according to the embodiment, and FIG. 3 is a cross-sectional view of a fine particle generating apparatus according to an embodiment. Referring to FIG. 1 to FIG. 3, an external power supply device 1000 according to an embodiment includes cases 200 that may be separated. Each of the cases 200 has a partitioned inside, so that elements of the external power supply device 1000 may be mounted, and includes a plurality of hooks 205 and protrusion recesses 206 to be coupled to each other. An auxiliary battery 400 and an auxiliary power supply device 500 may be mounted in an accommodation portion 401 of the external power supply device 1000, and a charging accommodation portion 30 may be mounted to the case 200 of the external power supply device 1000 by inserting a hinge 303 to a groove 202 formed in the case 200, wherein the hinge 303 is provided through holes 301 formed in opposite surfaces of the charging accommodation portion 300. The charging accommodation portion 300 is configured to accommodate the fine particle generating apparatus 100, the auxiliary power supply device 500 is connected to the auxiliary battery 400 via wires, and the auxiliary power supply device 500 is connected to a charging terminal 302 provided in the charging accommodation portion 300 via wires 207. The auxiliary power supply device 500 controls the auxiliary battery 400 to be charged by a general external power source built in a case such as a universal serial bus (USB) port 506, and displays a charging status of the auxiliary battery 400 through a light-emitting diode (LED) 501. For example, referring to FIG. 1, the LED 501 includes three LEDs so as to turn on one LED, two or three LEDs according to the charged amount, and when the three LEDs are turned on, the auxiliary power storage device 400 is at the maximum charging status. Each LED in the LED 501 may be turned on to outside of the case through a hole 505 provided in the case 200 that is coupled to the case 200 in which the LED 501 is mounted. Also, the case 200 includes a button 503 protruding to the outside of the case 200 through a hole 504, and the button 503 is supported by a fixing protrusion 502 in the case 200. The button 503 is connected to the auxiliary power supply device 500 via a wire. When the button 503 is pushed in a state where the fine particle generating apparatus 100 is accommodated in the charging accommodation portion 300 perpendicularly to the case, the auxiliary power supply device 500 applies heat to a opening of the fine particle generating apparatus 100 through the charging terminal 302 of the charging accommodation portion 300 to clean the fine particle generating apparatus 100 by melting dust or impurities on the fine particle generating apparatus 100. When the button 503 is pushed in a state where the fine particle generating apparatus 100 is accommodated in the charging accommodation portion 300 being inclined with respect to the case 200, the auxiliary power supply device 500 supplies the power of the auxiliary battery 400 to the fine particle generating apparatus 100 through the charging terminal 302 of the charging accommodation portion 300 to pre-heat the fine particle generating apparatus 100. The charging terminal 302 of the charging accommodation portion 300 is connected to a charging terminal 30 provided in the fine particle generating apparatus 100 to face the charging terminal 302 in a state where the fine particle generating apparatus 100 is accommodated in the charging accommodation portion 300, and the power charged in the auxiliary battery 400 may be supplied to the fine particle generating apparatus 100 according to the control of the auxiliary power supply device 500. The auxiliary power supply device 500 includes a wireless communication port so as to supply the power wirelessly to the fine particle generating apparatus 100, as well as through wires.

Also, the case 200 includes a magnet 201, and the charging accommodation portion 300 includes a magnet at a predetermined location facing the magnet 201 to be mounted to the case 200 by the magnetic force. Also, a magnet 204 is provided on a lower portion of the case 200 to be inclined, and thus the fine particle generating apparatus 100 may be accommodated in the charging accommodation portion 300 by the magnetic force with respect to a magnet 60 that is provided in the fine particle generating apparatus 100 at the same height as that of the magnet 204.

FIG. 3 is a cross-sectional view showing main elements of the fine particle generating apparatus according to the embodiment. Referring to FIG. 3, the fine particle generating apparatus according to the embodiment includes a button 40 that is pushed to pre-heat the fine particle generating apparatus, a heater 20 generating heat due to resistance after receiving applied current, a power storage device 70 capable of instantly supplying high power to the heater 20, and a control device 50 controlling the heater 20. The heater 20 generates fine particles a vaporizing material including a material (vaporizing material) that vaporizes when being heated to a predetermined temperature or greater accommodated in a cartridge 10. For example, when an electronic tobacco of a cigarette type filled with paper impregnated or coated with an inhalation material is inserted to the cartridge 10, the heater 20 is heated to vaporize the inhalation material in a cigarette portion and a user may inhale the inhalation material that is vaporized through a filter portion. When the fine particle generating apparatus 100 does not operate and needs to be charged because the heater 20 lacks electric power or when the fine particle generating apparatus 100 is ready to operate, the control device 50 drives a motor 80 to vibrate the fine particle generating apparatus 100 so that the user may recognize it. Also, the control device 50 display a remaining power of the power storage device 70 via an additional display unit provided in the fine particle generating apparatus 100, and even when the fine particle generating apparatus 100 is impossible to operate because the heater 20 lacks the electric power, the status may be displayed through the display unit. The power storage device 70 is connected to the charging terminal 30 of the fine particle generating apparatus 100 via wires to receive the power supply, wherein the charging terminal 30 is connected to the charging terminal 302 of the charging accommodation portion 300 in a state where the external power supply device 1000 is accommodated in the charging accommodation portion 300, and when the fine particle generating apparatus 100 receives the power supply, the control device 50 may display the electric power supplied to the power storage device 70 through the display unit. The fine particle generating apparatus 100 may perform data communication with the charging terminal 302 of the external power supply device 1000 via the charging terminal 30. Also, the fine particle generating apparatus 100 may include an additional wireless communication port so as to receive the electric power supply wirelessly from the external power supply device 1000, because the control device 50 may perform the data communication with the auxiliary power supply device 500 via the wireless communication port in the fine particle generating apparatus 100 and the wireless communication port in the external power supply device 1000. The power storage device 70 may be separated from the fine particle generating apparatus 100, and the external power supply device 1000 includes a plurality of accommodation portions for accommodating the power storage device 70 so that one or more power storage devices 70 separated from the fine particle generating apparatus 100 may be accommodated and charged therein. Also, the fine particle generating apparatus 100 according to the embodiment may include a power-generation unit that converts external energy such as optical energy or mechanical energy into electrical energy to charge the power storage device 70.

Figure 4:
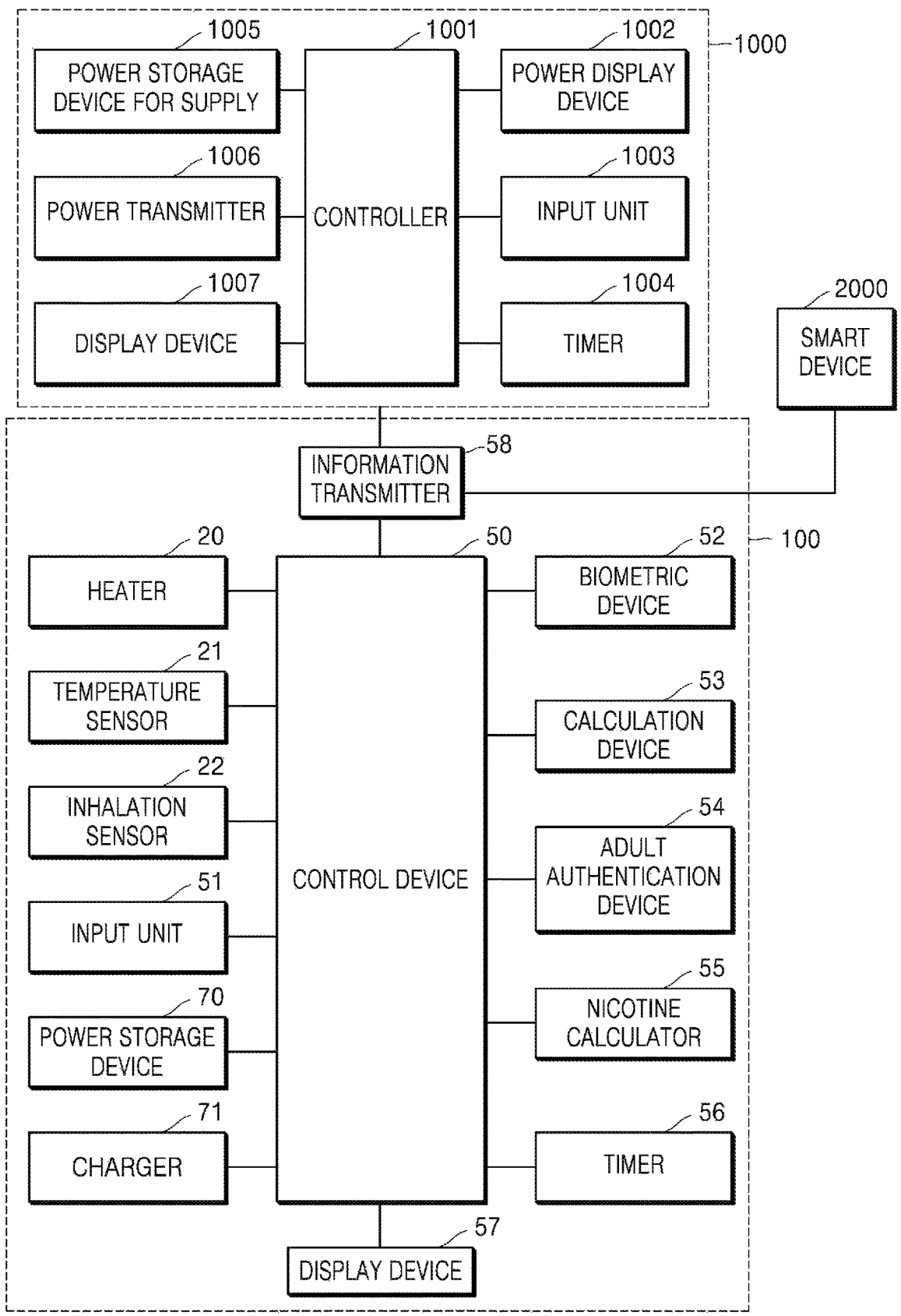
FIG. 4 is a block diagram of a fine particle generating apparatus according to an embodiment.

FIG. 4 is a schematic block diagram of a fine particle generating apparatus according to an embodiment. Referring to FIG. 4, the fine particle generating apparatus according to the embodiment generates fine particles so that the fine particles are inhaled through a puff of a user, and the fine particle generating apparatus includes the heater 20 generating heat due to resistance when receiving electric current, the power storage device 70 capable of instantly supplying high electric power to the heater 20, a display device 57 displaying usage information of the user, and the control device 50 controlling at least one of the above-stated elements. The heater 20 generates fine particles a vaporizing material including a material that vaporizes when being heated to a predetermined temperature or greater (vaporizing material). The heater 20 according to the embodiment may generate aerosol by using electricity. The heater 20 may generate fine particles and/or aerosol by converting the electricity supplied from the power storage device 70 into thermal energy.

The fine particle generating apparatus according to the embodiment includes a temperature sensor 21 for measuring the temperature of the heater 20, and a calculation device 53 that senses an instant temperature variation rate of the heater 20 to determine whether a puff of the user occurs or not. The temperature sensor 21 senses the temperature. For example, the temperature sensor 21 may sense the temperature of the heater 20. In this case, the temperature sensor 21 may determine an instant temperature variation rate (e.g., a temperature variation amount per unit time) of the heater 20. According to a detailed type of implementing the fine particle generating apparatus 100, the temperature variation amount per unit time of the heater may be determined by the temperature sensor 21, by the calculation device 53 or by the control device 50. When it is determined that there is a puff of the user by the calculation device 53, the control device 50 counts the number of puffs. The control device 50 displays usages information, e.g., the number of daily uses of the fine particle generating apparatus, through the display device 57. Here, one time use may be defined as the number of puffs or a used time period. As shown in FIG. 4, the calculation device 53 may be implemented as a separate element from the control device 50. However, the calculation device 53 may be included in the control device 50. According to an embodiment, the control device 50 may execute all operations performed in the calculation device 53, and when the control device 50 may execute the operations performed in the calculation device 53, the calculation device 53 may be omitted. Also, the control device 50 may perform the operations performed by a biometric device 52, an adult authentication device 54, a nicotine calculator 55, a timer 56, etc. that are provided as separate elements in FIG. 4, and in this case, each of the above-stated elements may be omitted. The control device 50 according to the embodiment may determine whether a puff occurs according to the sensed temperature variation amount per unit time. The control device 50 may determine whether the puff occurs according to a size or a variation in the temperature variation amount per unit time of the heater 20. For example, when the temperature variation amount per unit time of the heater 20 is equal to or greater than a first value that is set in advance, the control device 50 may determine that the puff has occurred. When there is the puff, an amount of external air inhaled per unit time is equal to or greater than a preset value, the temperature variation amount per unit time of the heater 20 may be equal to or greater than a predetermined level. Therefore, when the temperature variation amount per unit time of the heater 20 is equal to or greater than the first value that is set in advance, the control device 50 may determine that the puff behavior of the user has occurred. In another example, when the temperature variation amount per unit time of the heater 20 is less than a second value that is set in advance, the control device 50 may determine that the puff does not occur. Even when there is no puff, the external air may be introduced into the fine particle generating apparatus 100. For example, when the user walks carrying the fine particle generating apparatus 100, the external air may be introduced into the fine particle generating apparatus 100. However, when there is no puff behavior, the amount of the external air inhaled per unit time is less than a preset value, the temperature variation amount per unit time of the heater 20 may be lower than a predetermined level. Therefore, when the temperature variation amount per unit time of the heater 20 is less than the second value that is set in advance, the control device 50 may determine that the puff behavior of the user has not occurred. In the above description, the first value and the second value may be equal to or different from each other. The first and second values may be set in advance, and if necessary, may be determined by the user or may be updated according to peripheral environment (e.g., peripheral temperature). Also, the control device 50 according to the embodiment may continuously or regularly determine whether the puff has occurred, but may determine whether the puff has occurred according to the temperature variation amount per unit time only when introduction of the external air is sensed by an inhalation sensor 22, etc. For example, when the inhalation sensor 22 senses the air introduced into the fine particle generating apparatus 100, the control device 50 obtains information indicating the temperature variation amount per unit time of the heater 20 from the temperature sensor 21 and determines whether the puff has occurred according to the temperature variation amount per unit time of the heater 20. According to an embodiment, the inhalation sensor 22 may determine whether the air is introduced into the fine particle generating apparatus 100 by using a velocity of the air introduced in the fine particle generating apparatus 100. In this case, when the velocity of the air introduced into the fine particle generating apparatus 100 is equal to or greater than a preset value, the temperature sensor 21 may sense the temperature variation amount per unit time of the heater 20. When the velocity of the air introduced in the fine particle generating apparatus 100 is equal to or greater than a preset value, the control device 50 may determine whether the puff has occurred according to the temperature variation amount per unit time of the heater 20. When the puff has occurred, the control device 50 according to the embodiment may generate the fine particles or aerosol by supplying the electric power to the heater 20. Also, when the puff has occurred, the control device 50 may update the stored number of uses and/or the number of puffs to be increased. The number of uses may denote the number of times that the fine particle generating apparatus 100 is used, and the number of puffs may denote the number of puffs. For example, one time use may include a plurality number of puffs. Also, as described later, one time use may be defined as the number of puff or a used time period. For example, a predetermined number of puffs may correspond to one time use, and in another example, operations during a predetermined time period may correspond to one time use. However, the number of uses or the number of puffs are not restricted to the above examples.

Also, according to the embodiment, when the fine particle generating apparatus 100 is turned on and a puff of the user occurs at least once within ten minutes after the turning-on of the fine particle generating apparatus 100, the control device 50 of the fine particle generating apparatus 100 increases the number of uses by 1. If necessary, the control device 50 may reset the number of daily uses of the fine particle generating apparatus 100 every day.

Also, according to the embodiment, the fine particle generating apparatus 100 may include a charging portion 71 for charging the power storage device 70 with external power, and may receive the external power from the external power supply device 1000. The external power supply device 1000 includes a power storage device for supply 1005, a power transmitter 1006 connected to the fine particle generating apparatus 100 through wires or wirelessly to transmit the electric power, a power display device 1002 displaying a remaining power of the power storage device for supply 1005, a display device 1007 displaying usage information of the fine particle generating apparatus 100, and a controller 1001 controlling at least one of the above-stated elements. The fine particle generating apparatus 100 includes an information transmitter 58 that transmits usage information to outside in order to transmit the usage information to the external power supply device 1000, and the external power supply device 1000 synchronizes the usage information with the fine particle generating apparatus 100 through wires or wirelessly when being connected to the fine particle generating apparatus 100. Therefore, the external power supply device 1000 may display on the display device 1007 the usage information transmitted from the fine particle generating apparatus 100. The display device 1007 may display various information according to control of the control device 50 or the controller 1001. For example, the display device 1007 may display the number of uses or the number of puffs. The number of uses or the number of puffs may be updated and may be recorded by the control device 50 or the controller 1001. The power storage device 70 according to the embodiment may denote a battery that may output electrical energy. In detail, the power storage device 70 may supply the power to one or more elements included in the fine particle generating apparatus 100. For example, the power storage device 70 may supply the electric power to the heater 20, the control device 50, the temperature sensor 21, the inhalation sensor 22, the display device 57, etc.

According to the embodiment, the external power supply device 1000 increases the number of using the fine particle generating apparatus 100 by 1 when the energy supplied to the fine particle generating apparatus 100 is equal to or greater than a certain amount, in particular, the energy consumed by at least one puff, and both the fine particle generating apparatus 100 and the external power supply device 1000 or one of the fine particle generating apparatus 100 and the external power supply device 1000 may include timers 56 and 1004 that measures time. Therefore, the time period of the puff of the user may be counted.

Also, according to the embodiment, both or one of the fine particle generating apparatus 100 and the external power supply device 1000 may include input units 51 and 1003 that reset the number of using the fine particle generating apparatus 100, and may reset the number of daily uses or designate a maximum number of daily uses, which is one piece of the usage information. In addition, the control device 50 of the fine particle generating apparatus 100 may block the electric power supplied from the power storage device 70 to the heater to prevent over-use of the heater.

According to the embodiment, the fine particle generating apparatus 100 synchronizes the usage information with a smart device 2000 by being connected to the smart device 2000 through wires or wirelessly. In addition, the smart device 2000 connected to the fine particle generating apparatus 100 through wires or wirelessly may analyze usage information, for example, the number of uses per day, and displays analyzation result such as an average number of daily uses for one month, etc. on the smart device 2000 itself or transfers the data to the fine particle generating apparatus 100 so that the fine particle generating apparatus 100 displays the above analyzation result on the display device 57 thereof.

According to the embodiment, the fine particle generating apparatus 100 may include the biometric device 52 such as an iris scanning device, a fingerprint recognition device, etc., and the control device 50 requests biometric information from the user through the display device 57 so that only the user certified by the biometric device 52 may control the fine particle generating apparatus 100 and corrects the usage information.

According to the embodiment, the fine particle generating apparatus 100 includes the adult authentication device 54, and the control device 50 may allow only the user authenticated as an adult by the adult authentication device 54 to control and use the fine particle generating apparatus 100. For example, the control device 50 forces a user who wants to use the fine particle generating apparatus 100 to pass through the authentication process of the adult authentication device 54 through the display device 57, and when the user is not authenticated as an adult from the adult authentication device 54, the control device 50 controls the heater 20 not to operate in order not to allow the user to use the fine particle generating apparatus 100. Therefore, a minor such as a youth or a kid is not allowed to use the fine particle generating apparatus 100. Also, according to the embodiment, the fine particle generating apparatus 100 includes the inhalation sensor 22 that senses an inhalation amount per one puff of the user, and the nicotine calculator 55 that calculates a nicotine puff amount that is one piece of the usage information based on the sensed inhalation amount, and then, displays the calculated information on the display device 57. Therefore, the user may not excessively perform the puff based on the calculation information. The inhalation sensor 22 according to the embodiment may sense the air introduced into the fine particle generating apparatus 100. The inhalation sensor 22 may sense the air applied to the fine particle generating apparatus 100 according to the puff. In addition, even when there is no puff operation, the inhalation sensor 22 may sense the air introduced into the fine particle generating apparatus 100. For example, even when the external air is simply introduced due to the shaking of the fine particle generating apparatus 100, the inhalation sensor 22 may sense the introduced air.

The controller 1001 or the control device 50 according to the embodiment may be implemented as a processor (not shown). The processor (not shown) is an element processing information or data, and may implement the controller 1001 or the control device 50.

Figure 5:
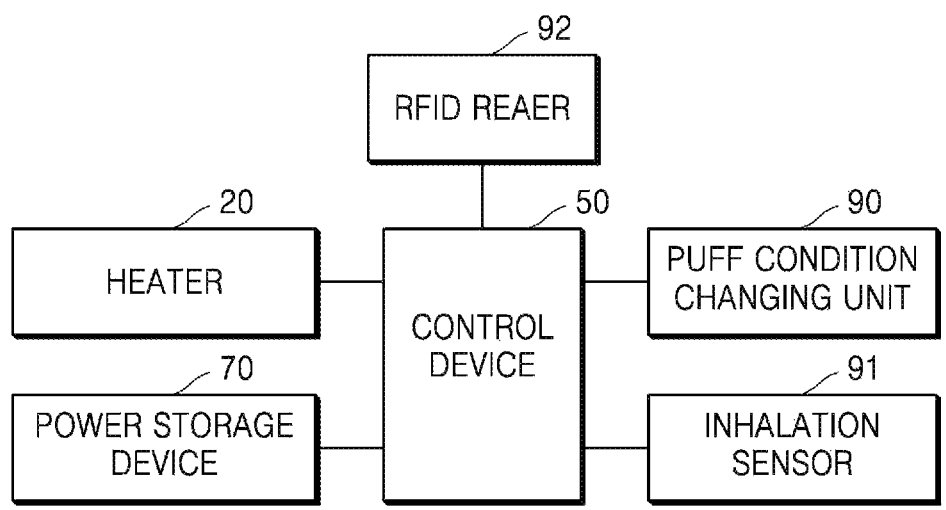
FIG. 5 is a block diagram of a fine particle generating apparatus according to an embodiment.

FIG. 5 is a block diagram of the fine particle generating apparatus according to an embodiment. Referring to FIG. 5, the fine particle generating apparatus 100 according to the embodiment includes the heater 20 that generates heat due to resistance when receiving the electric current applied thereto, the power storage device 70 supplying an instantly high electric power to the heater 20, a puff condition changing unit 90 that may change puff conditions of the fine particles, and the control device 50 controlling at least one of the above-stated elements. The heater 20 generates fine particles a vaporizing material including a material (vaporizing material) that vaporizes when being heated to a predetermined temperature or greater.

The puff condition changing unit 90 includes an input device, and thus, the user inputs the puff condition through the input device and changes the input puff condition. The puff condition changing unit 90 may change the puff condition in a manner of selecting one of at least two puff conditions. The puff condition includes the temperature of the heater 20 as an element to adjust the temperature, and the control device 50 maintains the temperature of the heater 20, which is selected as the puff condition. For example, the user may set the puff conditions such as a set temperature, a temperature maintaining time, etc. according to a kind of the vaporizing material through the puff condition changing unit 90. Therefore, when the user uses the fine particle generating apparatus 100, the fine particle generating apparatus 100 may be operated at a temperature, by which a satisfying puff feeling may be provided according to the kind of the vaporizing material.

Also, according to the embodiment, the puff condition may include an inhalation amount per at least one puff of the user as an element, and an inhalation sensor 91 that senses an inhalation amount per one puff of the user may be provided. Therefore, the control device 50 may sense the inhalation amount by using the inhalation sensor 91 to predict the temperature of the heater 20, which decreases due to the puff of the user, and then, controls the power supply so that the temperature of the heater 20 may be retained constantly and adjusts an atomization amount.

The control device 50 according to the embodiment obtains a sensing result of the air applied to the fine particle generating apparatus 100 according to the puff from the inhalation sensor 91, and may control the power supply to the heater 20 according to the sensing result obtained from the inhalation sensor 91. In detail, the control device 50 may control the power supply to the heater so that the temperature of the heater 20 may be maintained within a predetermined range. For example, the control device 50 determines a predicted decreasing temperature of the heater 20 according to the inhalation amount per one puff of the user, and controls the power supply to the heater 20 according to the determined predicted decreasing temperature in order to maintain the temperature of the heater 20 within a predetermined range. As an example, the control device 50 may control the power supply to the heater 20 so that the electric power is supplied to the heater 20 before the temperature of the heater 20 decreases to a predetermined temperature or lower due to the air applied to the fine particle generating apparatus 100 according to the puff or the puff of the user. The control device 50 may control the heater 20 by using the information obtained from the inhalation sensor 91. The control device 50 may control the electric power supplied to the heater 20 according to the information obtained from the inhalation sensor 91. For example, the control device 50 obtains from the inhalation sensor 91 information about an amount of the air, a temperature of the air, a velocity of the air applied to the fine particle generating apparatus 100 according to the puff, and controls the power supply to the heater 20 so that the temperature of the heater 20 may be maintained within the predetermined range based on the information obtained from the inhalation sensor 91.

The control device 50 may adjust the atomization amount by adjusting the temperature retaining time of the heater 20, as well as the temperature of the heater 20. The inhalation sensor 91 may obtain information about the air applied to the fine particle generating apparatus 100 according to the puff. For example, the inhalation sensor 91 may sense the amount of the air, the temperature of the air, the velocity of the air applied to the fine particle generating apparatus 100 according to the puff, etc. Also, the inhalation sensor 91 may provide the control device 50 with data. The data sensed by the inhalation sensor 91 may be transferred to the control device 50.

According to the embodiment, the vaporizing material including a plurality of vaporizing materials having different minimum vaporization temperatures from one another may be used, and at least some of the plurality of vaporizing materials may include nicotine and some of which may have different content of nicotine from one another. The user may select or change the puff condition through the input device of the puff condition changing unit 90 as described above, according to the kind of the vaporizing material taking into account the kinds of the vaporizing materials, nicotine content, etc.

Also, according to the embodiment, the fine particle generating apparatus includes a radio frequency identification (RFID) reader 92 that may recognize an RFID tag that may be included in the vaporizing material. The RFID tag may include information about the kind of the vaporizing material, the vaporizing materials, and nicotine content, and the control device 50 may switch to an optimal temperature control profile according to the information about the vaporizing material recognized via the RFID reader 92. Therefore, the control device 50 may provide the user with the optimal atomizing amount and the puff experience by controlling the heater 20 according to the switched optimal temperature control profile. The control device 50 determines the temperature control profile with respect to the heater 20 according to the sensing result of the air applied to the fine particle generating apparatus 100 according to the puff, and controls the power supply to the heater 20 according to the determined temperature control profile. The heater may generate aerosol according to the control of the control device 50. In detail, the control device 50 may determine one temperature control profile corresponding to the sensing result, from among a plurality of temperature control profiles. For example, the control device 50 may determine a temperature control profile corresponding to an inhalation amount per one puff of the user, from among the plurality of temperature control profiles. In another example, the control device 50 may determine one temperature control profile from among the plurality of temperature control profiles, based on at least one of an amount of the air, the temperature of the air, and the velocity of the air sensed by the inhalation sensor 91. The control device 50 determines the temperature of the heater 20, the temperature retaining time, and the temperature variation rate according to the time to correspond to the determined temperature control profile, and then operates the fine particle generating apparatus 100 according to the temperature control profile determined according to the sensing result of the air applied to the fine particle generating apparatus 100 according to the puff to provide satisfying puff experience to the user. For example, the fine particle generating apparatus 100 determines the vaporizing material that is currently used after sensing the air applied to the fine particle generating apparatus 100 according to the puff, and then operates in the temperature control profile corresponding to the determined vaporizing material. In another example, when the user strongly inhales three times at an initial stage of smoking, the fine particle generating apparatus 100 may operates in the temperature control profile in an over-heating mode. According to the embodiment, various vaporizing materials may be used, for example, a vaporizing material including a vaporizing material that is harmless to human body, a vaporizing material including a vaporizing material that is good for health, a vaporizing material including a material having pharmacological action with respect to the human body, a vaporizing material including phytoncide, etc. may be used, and the temperature control profile may be set in advance according to the kind of the vaporizing material or the user may select the puff condition to use the fine particle generating apparatus 100.

The control device 50 according to the embodiment may be implemented as a processor (not shown). The processor (not shown) is an element processing information or data, and may implement the control device 50.

Figure 6:
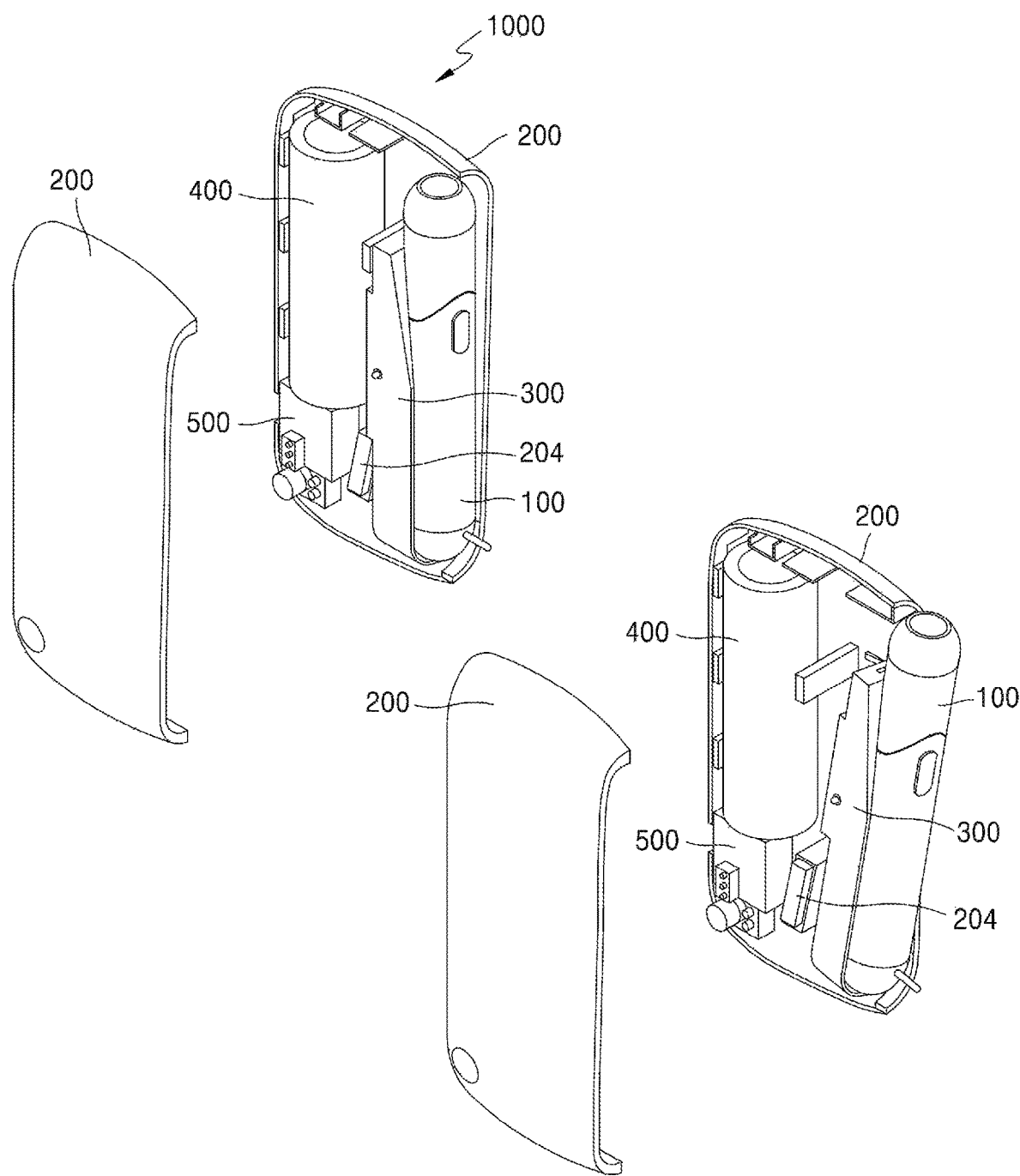
FIG. 6 is a perspective view showing that a fine particle generating apparatus according to an embodiment is ready to be used in a state of being accommodated in an external power supply device.

FIG. 6 is a perspective view showing that a fine particle generating apparatus according to an embodiment is ready to be used in a state of being accommodated in an external power supply device. Referring to FIG. 6, the fine particle generating apparatus 100 is accommodated in the charging accommodation portion 300 of the external power supply device 1000 to be supplied with the electric power. When the user wants to use the fine particle generating apparatus 100, the user pushes a lower end portion of the fine particle generating apparatus 100 in a state where the fine particle generating apparatus 100 is accommodated in the charging accommodation portion 300 of the external power supply device 1000 via the magnet 60 and the charging accommodation portion 300 is attached to the magnet 204 inclined by a predetermined angle in the case in a state where the fine particle generating apparatus 100 is accommodated in the charging accommodation portion 300 via the magnet 60 of the fine particle generating apparatus 100. Accordingly, an upper part of the fine particle generating apparatus 100 partially protrudes from the case 200 to be inclined by a predetermined angle, and the user inserts the electronic tobacco of the cigarette type into the cartridge 10 of the fine particle generating apparatus and pushes the button 503 on the external power supply device 1000 to pre-heat and use the fine particle generating apparatus 100. Therefore, the fine particle generating apparatus 100 may be continuously used while receiving the electric power from the external power supply device 1000.

Figure 7:
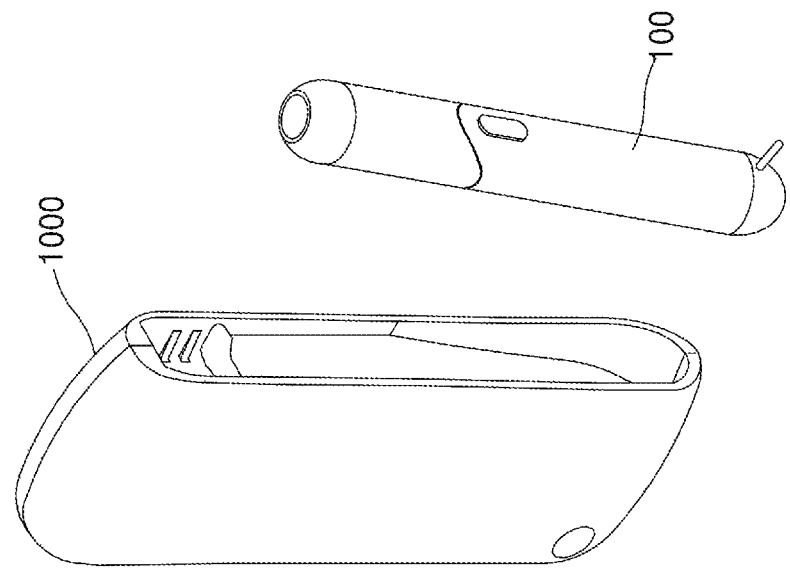
FIG. 7 is a perspective view showing a process of separating the fine particle generating apparatus according to an embodiment from an external power supply device.
Figure 7:
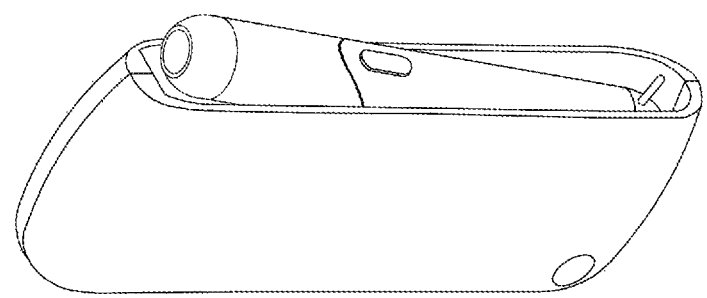
Figure 7:
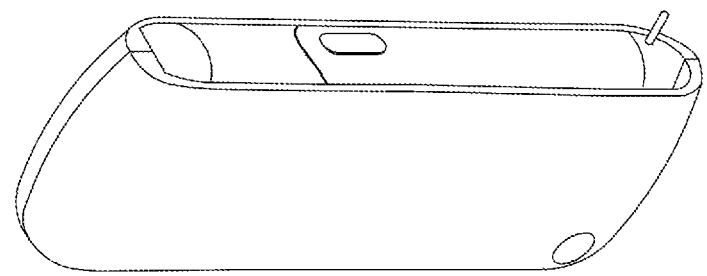
Figure 8:
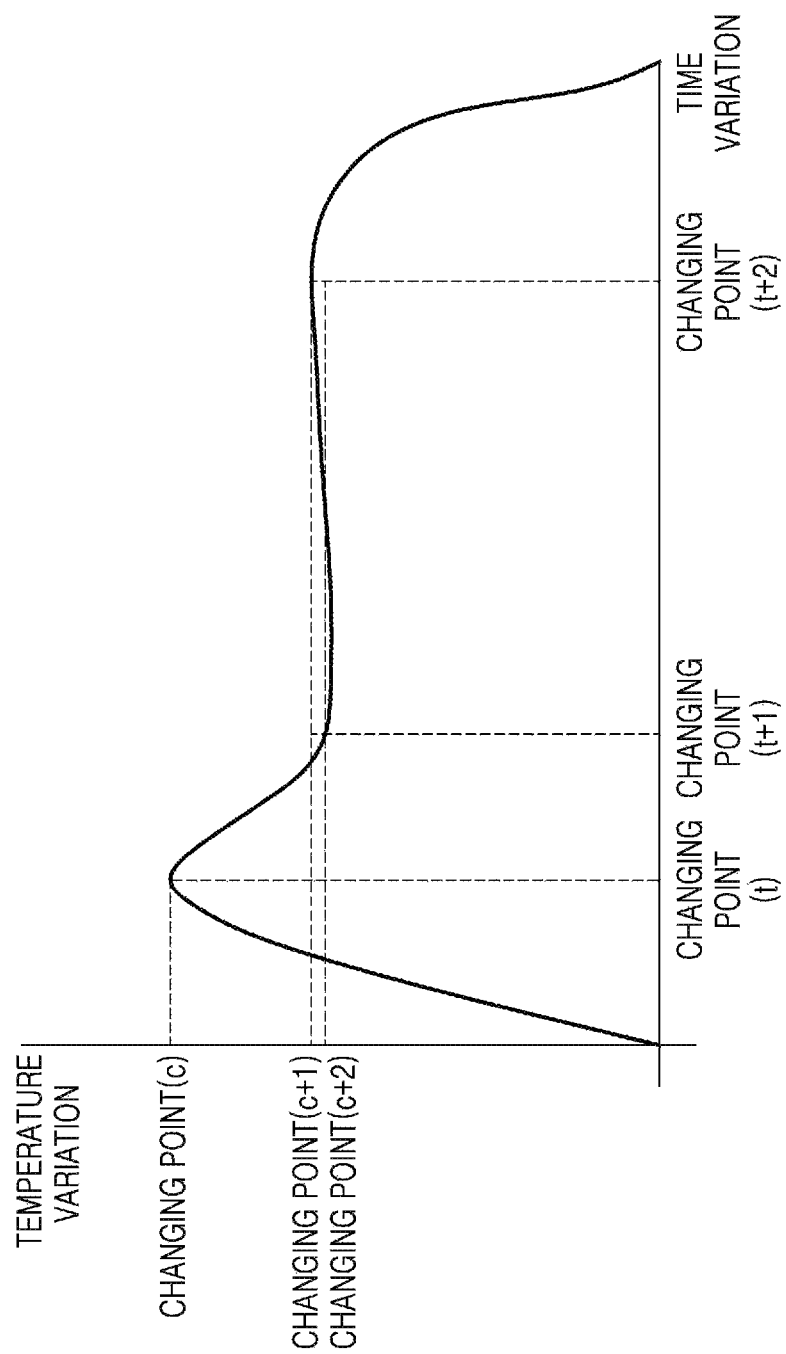
FIG. 8 is a schematic diagram showing a temperature control characteristic of an electronic tobacco according to the related art.

FIG. 7 is a perspective view showing a process of separating the fine particle generating apparatus according to an embodiment from an external power supply device. Referring to FIG. 7, when the user separates the fine particle generating apparatus from the external power supply device, the user may apply force to the fine particle generating apparatus 100 in a state where the fine particle generating apparatus 100 is partially exposed as inclined with respect to the external power supply device 1000 and withdraw the fine particle generating apparatus 100 while overcoming the magnetic force between the fine particle generating apparatus 100 and the external power supply device 1000.

Figure 9:
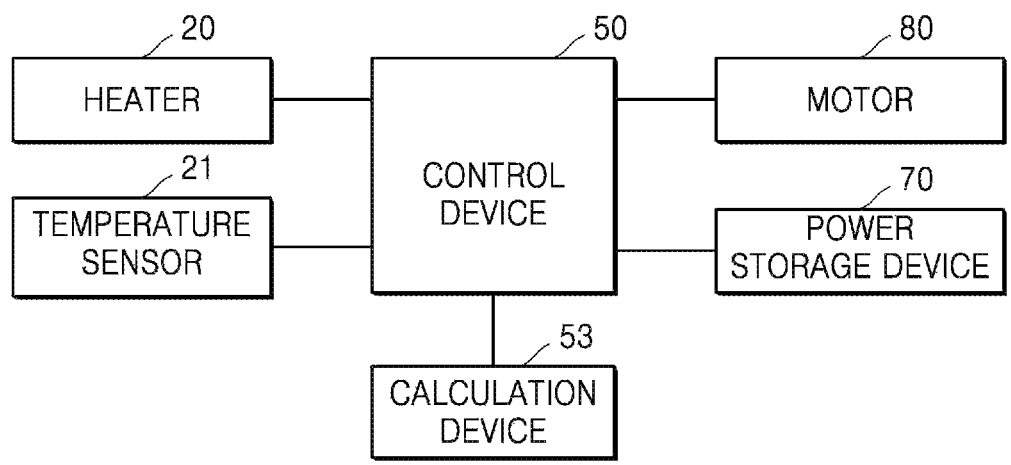
FIG. 9 is a block diagram showing a hardware configuration of the fine particle generating apparatus of FIG. 3.

FIG. 9 is a block diagram of a hardware configuration of the fine particle generating apparatus according to the embodiment. Referring to FIG. 9, the fine particle generating apparatus 100 according to the embodiment includes the heater 20 generating heat due to the resistance on receiving the electric current, the power storage device 70 capable of instantly supplying high electric power to the heater, and the control device 50 for controlling the heater. The heater 20 generates fine particles a vaporizing material including a material that vaporizes when being heated to a predetermined temperature or greater (vaporizing material), and in particular, the fine particles may include particles that is fine enough to float in the art, that is, aerosol. The vaporizing material may be in a liquid or solid phase, and the vaporizing material may include, for example, nicotine, or a material having a certain favor or flavor. The control device 50 controls the heater 20 to heat the vaporizing material at a burning temperature of the vaporizing material or less so as not to burn the vaporizing material, and when the fine particle generating apparatus 100 operates, the heater 20 is controlled in a pre-heating stage, a vaporizing temperature reaching state, and a vaporizing temperature retaining stage. The control device 50 heats the heater 20 to a temperature that is less than the burning temperature but close to the burning temperature of the vaporizing material in the pre-heating stage. In the vaporizing temperature reaching stage, the control device 50 stops supplying the electric power to the heater 20 so that the temperature of the heater 20 may decrease to a minimum vaporizing temperature of the vaporizing material, and in the vaporizing temperature retaining stage, the control device 50 controls the temperature of the heater 20 to be maintained between a maximum vaporizing temperature, at which a vaporizing amount of the vaporizing material reaches maximum, and the minimum vaporizing temperature. The control device 50 supplies the electric power to the heater 20 when the temperature of the heater 20 reaches the minimum vaporizing temperature and stops supplying the electric power to the heater 20 when the temperature of the heater 20 reaches the maximum vaporizing temperature, and thus, the control device 50 may efficiently manages the electric power. Also, according to the embodiment, when a temperature dropping rate of the heater 20 increases, the calculation device 53 of the fine particle generating apparatus 100 may recognize that the puff of the user has occurred. When the occurrence of the puff of the user is recognized, the control device 50 supplies the heater 20 with the maximum power to heat the heater 20 to the maximum vaporizing temperature. Also, when the calculation device 53 does not recognize the occurrence of the puff of the user after the fine particle generating apparatus 100 is operated for a predetermined time period, the control device 50 blocks the supply of the electric power to the heater 20 to prevent unnecessary power consumption. According to the embodiment, the fine particle generating apparatus 100 includes the temperature sensor 21 that measures the temperature of the heater 20, and the temperature sensor 21 is attached to the heater 20 to sense the temperature of the heater 20 by sensing a variation in the thermal resistance of the heater 20.

According to the embodiment, the heater 20 of various shapes having an excellent thermal conduction efficiency may be applied. For example, the heater 20 may have a needle shape or a pentagonal plane shape taking into account the thermal conduction efficiency.

Also, according to the embodiment, the heater 20 may be manufactured as a cylindrical shape with a hollow therein in order to use the electronic tobacco of a cigarette type which is impregnated or coated with the vaporizing material. The electronic tobacco of the cigarette type includes a filter portion and a cigarette portion including the vaporizing material. When the electronic tobacco is inserted in the fine particle generating apparatus 100, the cigarette portion including the vaporizing material is inserted in the hollow of the heater 20, and when the heater 20 is heated and vaporizes the vaporizing material in the cigarette portion, the user may inhale the inhalation material that is vaporized through the filter portion.

Figure 10:
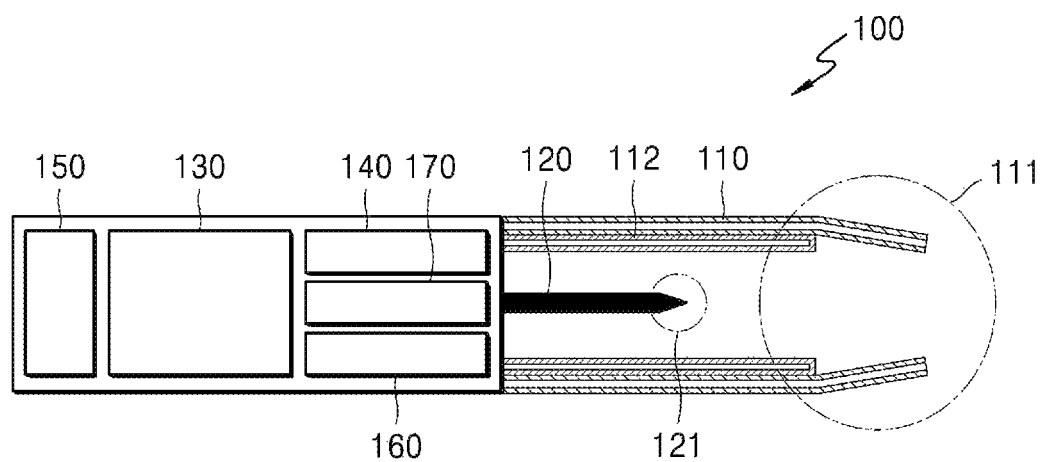
FIG. 10 is a cross-sectional view of a fine particle generating apparatus according to another embodiment.
Figure 11:
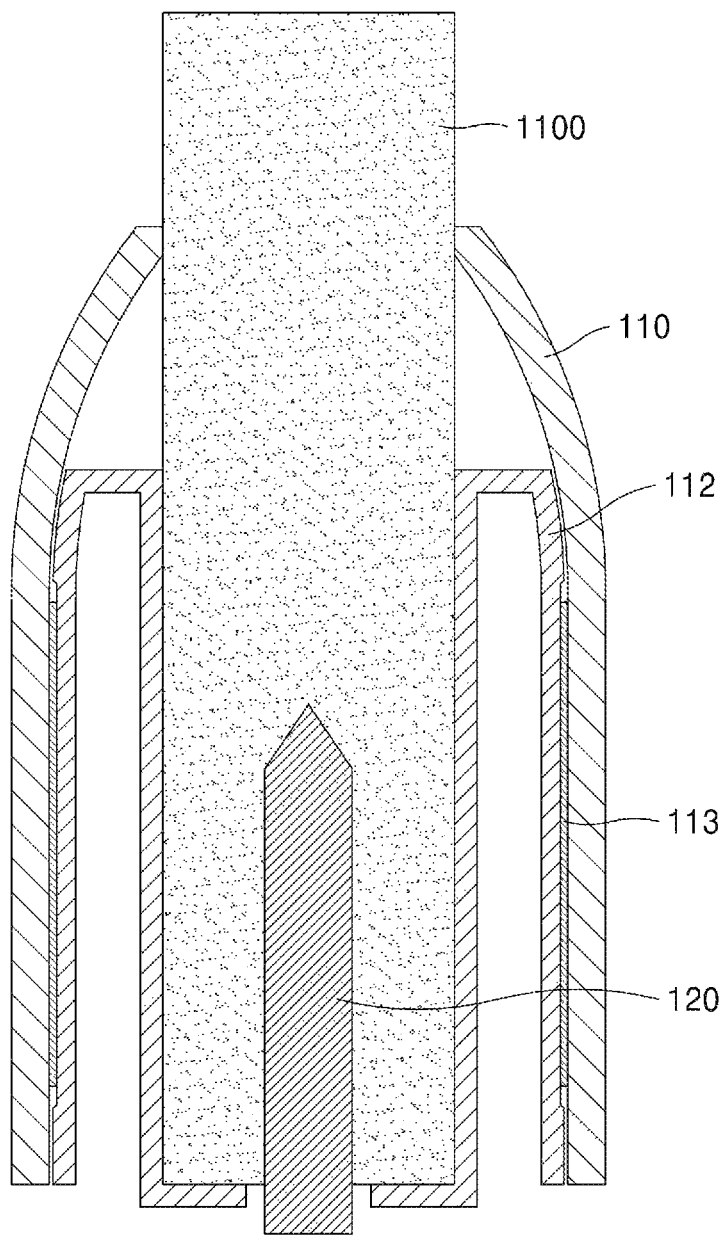
FIG. 11 is a cross-sectional view showing an example of inserting a cigarette to a case of the fine particle generating apparatus of FIG. 10.

FIG. 10 is a cross-sectional view of a fine particle generating apparatus according to another embodiment, and FIG. 11 is a cross-sectional view showing an example in which a cigarette is inserted into a case of the fine particle generating apparatus of FIG. 10.

Referring to FIG. 10 and FIG. 11, the fine particle generating apparatus 100 according to the embodiment may include a case 110, a heater 120, a battery 130, an input unit 140, a motor 150, a charger 160, and a processor 170. Also, the fine particle generating apparatus 100 may include an inner space formed by the case 110. A cigarette 1100 may be inserted to the inner space of the fine particle generating apparatus 100.

In the fine particle generating apparatus 100 of FIGS. 9 and 10, elements related to the embodiment are only shown. Therefore, one of ordinary skill in the art would appreciate that other universal elements than the elements shown in FIGS. 9 and 10 may be further included in the fine particle generating apparatus 100.

When the cigarette 1100 penetrates through the heater 120 in the case 110 of the fine particle generating apparatus 100, that is, the cigarette 1100 is inserted to the fine particle generating apparatus 100, the fine particle generating apparatus 100 may heat the heater 120. The vaporizing material including the vaporizing material in the cigarette 1200 has a temperature that is increased by the heater 120, and the vaporizing material heated to a predetermined temperature or greater may generate fine particles (e.g., aerosol). For example, when an electronic tobacco, e.g., the cigarette 1100 filled with paper impregnated or coated with a inhalation material is inserted to the cartridge 110, the heater 120 is heated to vaporize the inhalation material in the cigarette 1100 and a user may inhale the inhalation material that is vaporized through a filter portion. However, even when the cigarette 1100 is not inserted to the fine particle generating apparatus 100, the heater 120 may be heated.

The case 110 may be separated from the fine particle generating apparatus 100. For example, when the user rotates the case 110 in a clockwise direction or a counter-clockwise direction, the case 110 may be separated from the fine particle generating apparatus 100.

A diameter of a hole configured by an end 111 of the case 110 may be smaller than that of a space configured by the case 110 and the heater 120, and in this case, the hole configured by the end 111 may guide the cigarette 1100 that is inserted to the fine particle generating apparatus 100.

A cigarette holder 112 supporting the cigarette 1100 that is inserted penetrating through the heater 120 may be provided between the case 110 and the heater 120. Also, an insulating member 113 that may reduce thermal loss of the heater 120 may be provided between the case 110 and the cigarette holder 112. The insulation member 113 may include an insulator such as a graphite sheet, a steel use stainless (SUS) (stainless steel), etc. In the embodiment, the insulation member 113 may be bonded to the cigarette holder 112, and the cigarette 112 to which the insulation member 113 is bonded may be assembled and integrated with the case 110. The insulation member 113 blocks radiation of the heat generated from the heater 120, and thereby reduces thermal loss when the electric power supplied to the heater 120 is blocked. When SUS is included in the insulation member 113, a thermal dispersion effect may be obtained.

The heater 120 may be heated by the electric power supplied from the battery 30. When the cigarette 1100 is inserted to the fine particle generating apparatus 100, the heater 120 is located in the cigarette 1100. Therefore, the heater 120 that is heated may increase a temperature of the vaporizing material in the cigarette 1100.

The heater 120 may has a shape combining a cylinder shape with a cone shape. A diameter of the heater 120 may be selected within a range of 2 mm to 3 mm. For example, the heater 120 may have a diameter of 2.15 mm, but is not limited thereto. Also, a length of the heater 120 may be within a range of 20 mm to 30 mm. Also, the length of heater 120 may be 19 mm, but is not limited thereto. Also, an end 121 of the heater 120 may be shaped to have an acute angle, but is not limited thereto. That is, the heater 120 may be formed in any kind of shape, provided that the heater 120 may be inserted in the cigarette 1100. Also, the heater 120 may be partially heated. For example, when the heater 120 has a length of 19 mm, a portion from the end 121 of the heater 120 to a point of 12 mm may be heated and remaining portion of the heater 120 may not be heated.

The heater 120 may be an electrically resistant heater. For example, the heater 120 may include an electrically conductive track, and when the electric current flows on the electrically conductive track, the heater 120 may be heated.

For stabilized use, the electric power according to a standard of 3.2 V, 2.4 A, and 8 W may be supplied to the heater 120, but is not limited thereto. For example, when the electric power is supplied to the heater 120, a surface temperature of the heater 120 may increase to 400□C or greater. Before 15 seconds elapse since the supply of electric power to the heater 120 has started, the surface temperature of the heater 120 may increase to about 350□C.

The battery 130 may supply the electric power used to operate the fine particle generating apparatus 100. For example, the battery 130 may supply the electric power to heat the heater 120, and the electric power that is necessary to operate the processor 170. Also, the battery 130 may supply the electric power that is necessary for operating a display unit (not shown), a sensor (not shown), the motor 150, etc. included in the fine particle generating apparatus 100.

The battery 130 may include $LiFePO_4$ battery, but is not limited thereto. For example, the battery 130 may include a lithium cobalt oxide ($LiCoO_2$) battery, a lithium titanate battery, etc.

Also, the battery 130 may have a cylindrical shape having a diameter of 10 mm and a length of 37 mm, but is not limited thereto. The battery 130 may have a capacity of 120 mAh or greater, and the battery 130 may be a rechargeable battery or a disposable battery. For example, when the battery 130 is rechargeable, a charging rate (C-rate) of the battery 130 may be 10 C and a discharging rate (C-rate) may be 16 C to 20C, but one or more embodiments are not limited thereto. For stabilized use, the battery 130 may be manufactured to ensure 80% or greater of total capacity, even after charging/discharging are performed 8000 times.

Here, fully charged state/fully discharged state of the battery 130 may be determined by the processor 170 depending on the level of the stored power on the battery 130 with respect to the total capacity of the battery 130. For example, when the power stored on the battery 130 is 95% or greater with respect to the total capacity, it may be determined that the battery 130 is fully charged. Also, when the power stored on the battery 130 is 10% or less with respect to the total capacity, it may be determined that the battery 130 is completely discharged. However, criteria on determining the fully charged state/fully discharged state of the battery 130 are not limited to the above examples.

The input unit 140 may include at least one button by which the user may control the functions of the fine particle generating apparatus 100. An input signal input through the input unit 140 is provided to the processor 170, and the processor 170 may execute various functions corresponding to input signals. The user may execute a desired function from among a plurality of functions, by adjusting the number of times of pushing the input unit 140 (e.g., one time, two times, etc.) or a time period of pushing the input unit 140 (e.g., 0.1 sec., 0.2 sec., etc.) When the user operates the input unit 140, the fine particle generating apparatus 100 starts operating and a function of pre-heating the heater 120, a function of adjusting the temperature of the heater 120, a function of cleaning a space in which the cigarette 1100 is inserted, a function of checking whether the fine particle generating apparatus 100 is available, a function of displaying a remaining capacity (available power) of the battery 130, a function of resetting the fine particle generating apparatus 100, etc. may be executed. However, functions of the fine particle generating apparatus 100 are not limited to the above examples.

The motor 150 is controlled by the processor 170 to vibrate. According to the status of the fine particle generating apparatus 100, for example, when the fine particle generating apparatus 100 is impossible to operate due to lack of the electric power in the heater 120 and needs to be charged, or when the fine particle generating apparatus 100 is ready for operating, the motor 150 is driven to vibrate the fine particle generating apparatus 100 and the user may recognize it.

The charger 160 may be controlled by the processor 170, and the fine particle generating apparatus 100 may perform data communication with an external power supply device via the charger 160 and receive the electric power from the external power supply device. In addition, when the fine particle generating apparatus 100 receives the electric power, the processor 170 may display the electric supplied to the battery 130 via a display unit. In the embodiment, data or programs that are stored in the memory (180 of FIG. 2) through the charger 160 connected to an external device (not shown, e.g., a user terminal or a related device on which an application related to the fine particle generating apparatus is loaded) may be updated.

The processor 170 may control overall operations of the fine particle generating apparatus 100. In detail, the processor 170 may check the status of each component in the fine particle generating apparatus 100 to determine whether the fine particle generating apparatus 100 is in an available state.

At least one processor 170 may be provided, and the processor 170 may be implemented as an array of a plurality of logic gates or a combination of a universal microprocessor and the memory 180 in which programs executable on the microprocessor are stored. In addition, one of ordinary skill in the art would appreciate that the central processor may be implemented other types of hardware.

For example, the processor 170 may control operations of the heater 120. The processor 170 may control the amount of the electric power and the time of supplying the electric power to the heater 120, so that the heater 120 may be heated to a predetermined temperature or may be maintained at an appropriate temperature. Also, the processor 170 may check the status of the battery 130 (e.g., remaining capacity of the battery 130), and may generate a notification signal if necessary.

The processor 170 may check whether there is a puff of the user and a strength of the puff, and count the number of puffs. The processor 170 may continuously check the time period of operating the fine particle generating apparatus 100.

In addition, the fine particle generating apparatus 100 may further include other universal components than the above components.

For example, the fine particle generating apparatus 100 may include a display unit for outputting visual information. For example, when the fine particle generating apparatus 100 includes a display unit, the processor 170 may show the user information about the status of the fine particle generating apparatus 100 (e.g., whether the fine particle generating apparatus is available, etc.), information about the heater 120 (e.g., start pre-heating, processing the pre-heating, finish pre-heating, etc.), information about the battery 130 (e.g., a remaining capacity of the battery 130, availability, etc.), information about reset of the fine particle generating apparatus 100 (e.g., reset time, reset processing, reset finishing, etc.), information about cleaning of the fine particle generating apparatus 100 (e.g., cleaning time, need to clean, cleaning processing, cleaning finished, etc.), information about charging of the fine particle generating apparatus 100 (e.g., need to charge, charge processing, charge finished, etc.), information about puff (e.g., the number of puffs, notice to finish the puff, etc.), or information about safety (e.g., expired service life, etc.). Here, the above-stated information is transferred to the motor 150 so that the user may recognize the status of the fine particle generating apparatus 100.

For example, the fine particle generating apparatus 100 may clean the space in which the cigarette 1100 is inserted by controlling the heater 120 as follows. For example, the fine particle generating apparatus 100 may clean the space in which the cigarette 1100 is inserted by heating the heater 120 to a sufficiently high temperature. Here, the sufficiently high temperature may denote a temperature suitable for cleaning the space for the insertion of the cigarette 1100. For example, the fine particle generating apparatus 100 may heat the heater 120 to the highest temperature within a temperature range, in which the fine particles may be generated from the cigarette 1100, and a temperature range for pre-heating the heater 120.

Also, the fine particle generating apparatus 100 may maintain the heater 120 at a sufficiently high temperature during a predetermined time section. Here, the predetermined time section may denote a time period that is sufficiently long enough to clean the space in which the cigarette 1100 is inserted. For example, the fine particle generating apparatus 100 may maintain the temperature of the heater 120 for an appropriate time period among a plurality of time sections of 10 sec. to 10 min., but one or more embodiments are not limited thereto. For example, the fine particle generating apparatus 100 may maintain the temperature of the heater 120 for an appropriate time period selected within a range of 20 sec. to one minute. For example, the fine particle generating apparatus 100 may maintain the temperature of the heater 120 for an appropriate time period selected within a range of 20 sec. to one min. and 30 sec.

Since the fine particle generating apparatus 100 heats the heater 120 to a sufficiently high temperature and maintains the temperature of the heater 120 for a predetermined time period, materials deposited on a surface of the heater 120 and/or in the space in which the cigarette 1100 is inserted may be evaporated and cleaned.

Also, the fine particle generating apparatus 100 may include a puff sensor and/or a cigarette insertion sensor. For example, the puff sensor may be implemented by using a general pressure sensor. Alternatively, the fine particle generating apparatus 100 may sense the puff via a variation in the resistance of the electrically conductive track included in the heater 120, without using an additional puff sensor. Here, the electrically conductive track may include an electrically conductive track for heating and/or an electrically conductive track for sensing temperature. Alternatively, the fine particle generating apparatus 100 may further include a puff sensor, in addition to the electrically conductive track in the heater 120, which senses the puff.

The cigarette insertion sensor may be implemented by using a general capacitive sensor or a resistor sensor. Also, the cigarette 100 may be manufactured to have a structure, in which external air may be introduced/discharged even in a state where the cigarette is inserted.

Figure 12:
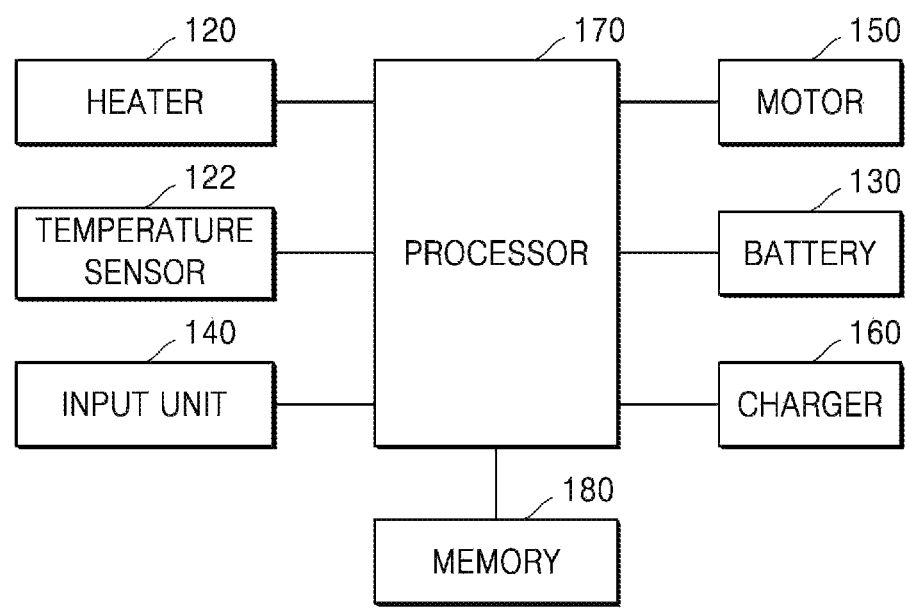
FIG. 12 is a block diagram of a hardware configuration of the fine particle generating apparatus of FIG. 10.
Figure 13:
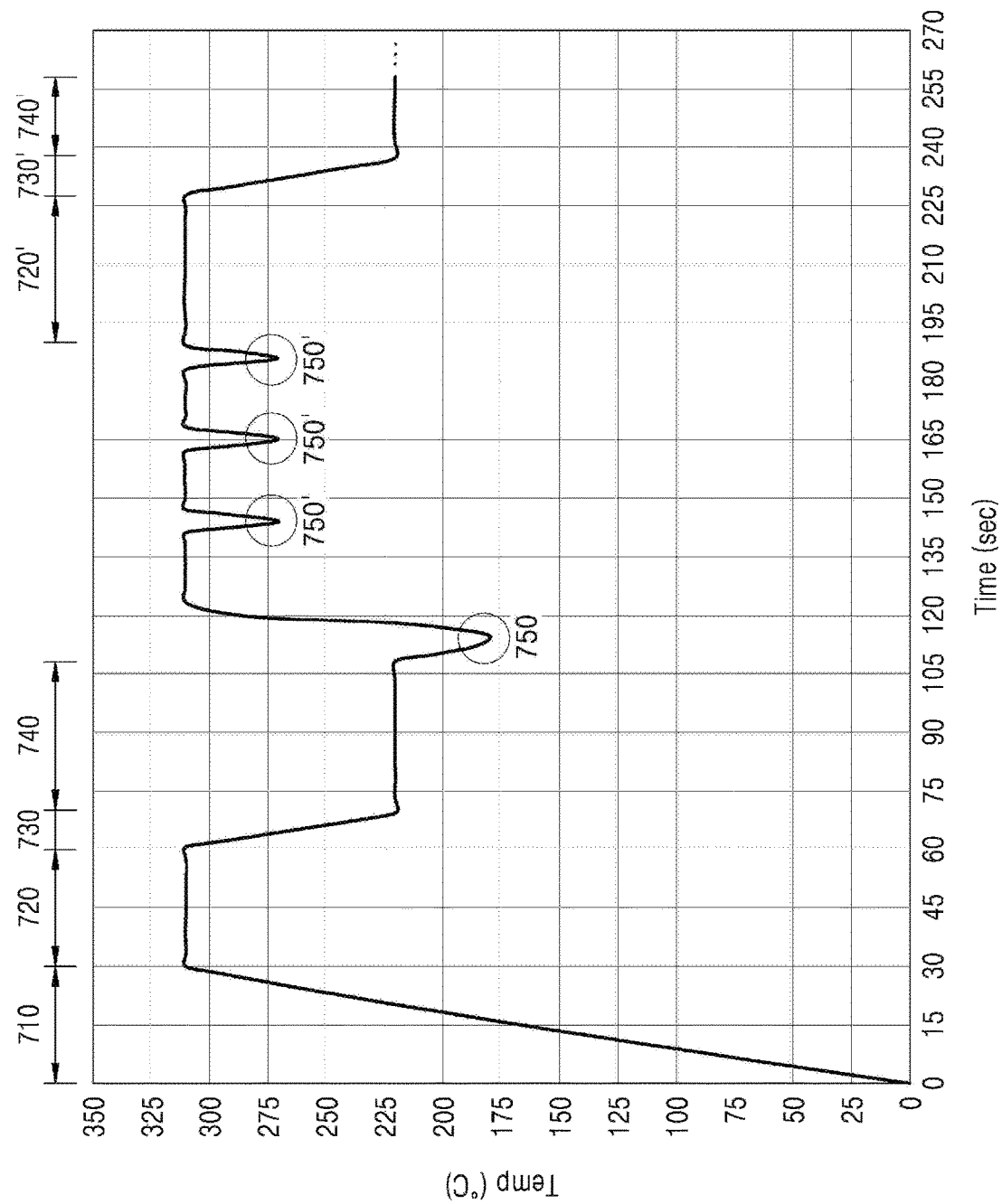
FIG. 13 is a graph of temperature profile information of a heater in the configuration of FIG. 12.

FIG. 12 is a block diagram of a hardware configuration of the fine particle generating apparatus of FIG. 10, and FIG. 13 is a graph showing temperature profile information of the heater of FIG. 12. Hereinafter, descriptions provided above with reference to FIGS. 10 and 11 are not provided.

Referring to FIG. 12, the fine particle generating apparatus 100 according to the embodiment may include the heater 120, the battery 130, the input unit 140, the motor 150, the charger 160, the processor 170, and the memory 180. In an alternative embodiment, the memory 180 may be included in the processor 170.

The heater 120 generates fine particles a vaporizing material including a material that vaporizes when being heated to a predetermined temperature or greater (vaporizing material), and in particular, the fine particles may include particles that is fine enough to float in the art, that is, aerosol. The vaporizing material may be in a liquid or solid phase, and the vaporizing material may include, for example, nicotine, or a material having a certain favor or flavor. The heater 120 operates with the electric power supplied from the battery 130, and the processor 170 executes an instruction stored in the memory 180 to adjust the energy supplied from the battery 130 and/or the heating time of the heater 120.

The temperature sensor 122 measures the temperature of the heater 120 and generates temperature measurement information, and then provides the temperature measurement information to the processor 170. In the embodiment, the temperature sensor 122 may be independently provided in the fine particle generating apparatus 100 to measure the temperature of the heater 120, or may be attached to the heater 120 to sense a variation in the thermal resistance and measure the temperature of the heater 120.

The memory 180 may store various data and programs for driving and controlling the fine particle generating apparatus 100. The program stored in the memory 180 may include one or more instructions. The program (one or more instructions) stored in the memory 180 may be accessed and executed by the processor 170. Here, when receiving an input signal for starting operation from the input unit 140, the processor 170 starts to access the memory 180 and executes the program (one or more instructions) stored in the memory 180.

The memory 180 according to the embodiment may include one or more instructions including temperature profile information for controlling the operation of the heater 120. Here, the temperature profile information denotes temperature information of the heater 120 based on time, and may include a pre-heating section (710 of FIG. 13), at least one vaporizing temperature retaining section (720 and 720' in FIG. 13), at least one vaporizing temperature descending section (730 and 730' in FIG. 13), at least one minimum vaporizing temperature retaining section (740 in FIG. 13), and at least one puff section (750 and 750' in FIG. 13). Each section may include information about the temperature that the heater 120 has to reach for a predetermined time period (e.g., in the pre-heating section, 310□C within 30 sec.)

The pre-heating section 710 may include a section for heating the heater 120 to a temperature close to the combustion temperature of the vaporizing material (e.g., 310□C). The vaporizing temperature retaining sections 720 and 720' may include a section in which the temperature of the heater 120 is maintained so that the vaporizing material may be vaporized. The vaporizing temperature descending sections 730 and 730' may include a section, in which the temperature of the heater 120 is descended to a minimum vaporizing temperature because the puff of the user is not sensed during the vaporizing temperature retaining section 720. The minimum vaporizing temperature retaining section (740 in FIG. 13) may include a section, in which the minimum vaporizing temperature so that the user may experience smoking flavor. The puff sections (750 and 750' in FIG. 13) may include a section in which a descending rate of the temperature of the heater 120 is greatly increased due to the puff of the user and a section in which the temperature of the vaporizing material is increased to the vaporizing temperature.

Also, the temperature profile information may include information about electric power supplied by the battery 130 to the heater 120 in correspondence with each section. For example, the information about the electric power may include information about adjusting the electric power of 100% to be supplied to the heater 120 in the pre-heating section 710, adjusting the electric power equal to or less than that of the pre-heating section 710 to be supplied to the heater 120 in the vaporizing temperature retaining sections 720 and 720', adjusting the electric power less than that in the vaporizing temperature retaining sections 720 and 720' to be supplied to the heater 120 so that the temperature descends to the minimum vaporizing temperature in the vaporizing temperature descending sections 730 and 730', adjusting the electric power equal to or greater than that supplied to the heater 120 when the temperature reached the minimum vaporizing temperature in the vaporizing temperature descending sections 730 and 730' to be supplied to the heater 120 in the minimum vaporizing temperature retaining section 740, and adjusting the electric power equal to or less than that of the vaporizing temperature retaining sections 720 and 720' to be supplied to the heater 120 so that the user inhales the fine particles in the puff sections 750 and 750'.

Also, the temperature profile information may include temperature measurement information of the heater 120 sent from the temperature sensor 122 to the processor 170, that is, reference information for determining what section the heater 120 is currently in. That is, the processor 170 compares the temperature measurement information with the reference information to determine where the heater 120 is currently located, and adjusts the electric power supplied to the heater 120 according to the determined section. For example, when the temperature measured by the temperature sensor 122 corresponds to the section in which the temperature rapidly drops with respect to the reference information, the processor 170 may determine that the temperature corresponds to the puff section, and thus, in the puff section, the electric power supplied to the heater 120 may be adjusted to heat the vaporizing material to the vaporizing temperature so that the user may inhale the fine particles.

FIG. 13 is a graph of the temperature profile information of the heater 120. Hereinafter, operations of the fine particle generating apparatus 100 of FIG. 12 will be described below with reference to FIG. 12.

When receiving an input signal for starting the operation from the input unit 140, the processor 170 accesses the memory 180 to execute one or more instructions stored in the memory 180.

In the pre-heating section 710, the processor 170 may heat the heater 120 to a temperature close to the combustion temperature of the vaporizing material (e.g., 310□C). In the pre-heating section 710, the processor 170 may operate the battery 130 so that 100% electric power is supplied to the heater 120 for a predetermined time period.

After finishing the pre-heating of the heater 120, the processor 170 may maintain the temperature of the heater 120 so that the vaporizing material is vaporized in the vaporizing temperature retaining section 720. In the vaporizing temperature retaining section 720, the processor 170 may operate the battery 130 so that the electric power equal to or less than that of the pre-heating section 710 may be supplied to the heater 120.

In the vaporizing temperature retaining section 720, when the puff of the user does not occur for a predetermined time period, the temperature control profile enters the vaporizing temperature descending section 730 in order to reduce the electric power consumed by the fine particle generating apparatus 100, and in the vaporizing temperature descending section 730, the processor 170 may operate the battery 130 so that the electric power less than that of the vaporizing temperature retaining section 720 is supplied to the heater 120 and the temperature descends to the minimum vaporizing temperature.

When the temperature of the heater 120 descends to the minimum vaporizing temperature in the vaporizing temperature descending section 730, the temperature control profile enters the minimum vaporizing temperature retaining section 740, and in the minimum vaporizing temperature retaining section 740, the processor 170 may operate the battery 130 so that the electric power equal to or greater than that supplied to the heater 120 when the temperature reaches the minimum vaporizing temperature during the vaporizing temperature descending section 730 may be supplied to the heater 120. Through the above operations, the electric power may be saved to 30% or less in the minimum vaporizing temperature retaining section as compared with that consumed in the vaporizing temperature retaining section 720.

When the temperature descending rate rapidly increases and the puff of the user is sensed during the minimum vaporizing temperature retaining section 740 and the temperature control profile enters the puff section 750, the processor 170 may operate the battery 130 so that the electric power equal to or less than that of the vaporizing temperature retaining section 720 may be supplied to the heater 120 and the user may inhale the fine particles.

After that, in the puff section 750' that may repeatedly occurs due to the puff of the user, the processor 170 may operate the battery 130 so that the electric power equal to or less than that of the vaporizing temperature retaining section 720 is supplied to the heater 120 and the user may inhale the fine particles. In the puff section 750' that repeatedly occurs, the temperature descending rate may have an inclination and an area that are equal to or less than those of the puff section 750 that has initially occurred.

After the last puff, the temperature control profile enters the vaporizing temperature retaining section 720', and in the vaporizing temperature retaining section 720', the processor 170 may operate the battery 130 so that the electric power equal to or less than that of the pre-heating section 710 may be supplied to the heater 120. Here, the vaporizing temperature retaining section 720' may be equal to or shorter than the previous vaporizing temperature retaining section 720, and may be reduced according to the number of puffs of the user.

In the vaporizing temperature retaining section 720', when the puff of the user does not occur for a predetermined time period, the temperature control profile enters the vaporizing temperature descending section 730' in order to reduce the electric power consumed by the fine particle generating apparatus 100, and in the vaporizing temperature descending section 730', the processor 170 may operate the battery 130 so that the electric power less than that of the vaporizing temperature retaining section 720' is supplied to the heater 120 and the temperature descends to the minimum vaporizing temperature. Here, the temperature in the vaporizing temperature descending section 730' may be equal to or higher than that of the previous vaporizing temperature descending section 730 in order to uniformly maintain generation of the fine particles from the cigarette 1100 that has been used, and the difference of the temperature may be related to the number of puffs.

In the embodiment, the vaporizing temperature retaining section, the vaporizing temperature descending section, the minimum vaporizing temperature retaining section, and the puff section may repeatedly occur.

The disclosure is not limited to the embodiments described above, and one of ordinary skill in the art, without departing from the subject matter of the disclosure claimed in claims, would carry out various modifications and such modifications are within the scope of the claims.

On the other hand, embodiments of the disclosure described above may be implemented in a general purpose digital computer to be written as a program that may be executed on a computer, and operate the programs using a computer readable recording medium. Also, structure of the data used in the above embodiments may be recorded on a computer-readable recording medium via various units. Examples of the computer readable recording medium include magnetic storage media (e.g., ROM, RAM, USB, floppy disks, hard disks, etc.), optical recording media (e.g., CD-ROMs, or DVDs), etc.

It will be understood by those of ordinary skill in the art that various changes in form and details may be made therein without departing from the spirit and scope of the disclosure as defined by the appended claims. The preferred embodiments should be considered in descriptive sense only and not for purposes of limitation. Therefore, the scope of the disclosure is defined not by the detailed description of the disclosure but by the appended claims, and all differences within the scope will be construed as being included in the present disclosure.

The invention claimed is:

1. An aerosol generating apparatus comprising:
   a heater configured to generate aerosol by using electricity;
   a processor configured to detect a puff based on a temperature variation amount per unit time of the heater, and control the heater to generate the aerosol based on detecting the puff;
   an inhalation sensor configured to sense an inhalation amount per one puff of a user;

a battery configured to supply electric power to the heater and the processor, wherein the processor is configured to predict a temperature of the heater to be decreased according to the inhalation amount, and control the battery to supply the electric power supplied to the heater based on the predicted temperature such that the temperature of the heater is maintained within a preset range.

2. The aerosol generating apparatus of claim 1, wherein the processor determines that the puff has occurred based on the temperature variation amount per unit time of the heater being equal to or greater than a preset value, and determines that no puff has occurred based on the temperature variation amount per unit time of the heater being less than the preset value.

3. The aerosol generating apparatus of claim 1, further comprising:

a temperature sensor configured to determine the temperature variation amount per unit time of the heater, wherein, based on the inhalation sensor sensing air introduced to the aerosol generating apparatus according to a puff, the processor obtains information indicating the temperature variation amount per unit time of the heater from the temperature sensor and determines whether the puff has occurred based on the information.

4. The aerosol generating apparatus of claim 3, wherein based on velocity of the air introduced into the aerosol generating apparatus being equal to or greater than a preset value, the temperature sensor begins sensing the temperature variation amount per unit time of the heater.

5. The aerosol generating apparatus of claim 1, wherein based on velocity of air introduced into the aerosol generating apparatus being equal to or greater than a preset value, the processor begins determining whether the puff has occurred according to the temperature variation amount per unit time of the heater.

6. The aerosol generating apparatus of claim 1, wherein based on the puff being detected, the processor updates previously stored information about a number of uses and/or a number of puffs by increasing the number of uses and/or the number of puffs.

7. The aerosol generating apparatus of claim 6, further comprising a display configured to display the number of uses and/or the number of puffs.

8. A fine particle generating apparatus of a heating type, the fine particle generating apparatus comprising:

a heater;

a battery configured to supply electric power to the heater;

a memory configured to store one or more instructions for controlling the heater; and a processor configured to operate the battery via the one or more instructions, wherein the one or more instructions comprise temperature profile information of the heater, the temperature profile information comprising (i) at least one vaporizing temperature retaining section for the heater, in which a vaporizing material is heated to a predetermined temperature or greater to discharge the vaporizing material, (ii) at least one vaporizing temperature decreasing section, in which a temperature of the heater is decreased to a minimum vaporizing temperature due to an absence of a puff, (iii) at least one minimum vaporizing temperature retaining section in which the minimum vaporizing temperature is maintained, and (iv) at least one puff section in which the temperature of the heater is decreased from the minimum vaporizing temperature due to an occurrence of the puff, and wherein the temperature profile information includes information about a temperature that the heater has to reach within a predetermined time period in each section, and information about the electric power supplied by the battery to the heater in correspondence with each section.

9. An aerosol generating apparatus comprising:

a heater;

a sensor including an inhalation sensor, the inhalation sensor being configured to sense an inhalation amount per one puff of a user;

a processor configured to predicts a temperature of the heater to be decreased according to the inhalation amount, and control electric power supplied to the heater based on the predicted temperature such that the temperature of the heater is maintained within a preset range.

10. The aerosol generating apparatus of claim 9, wherein the processor controls the electric power supplied to the heater such that the electric power is supplied to the heater before the temperature of the heater decreases to a predetermined level due to an air introduced into the aerosol generating apparatus.

11. The aerosol generating apparatus of claim 9, wherein the sensor further senses a temperature of an air introduced into the aerosol generating apparatus according to the puff, or velocity of the air, and the processor controls the electric power supplied to the heater further based on the temperature of the air, and the velocity of the air.

12. An aerosol generating method comprising:

sensing an inhalation amount per one puff of a user; and predicting a temperature of a heater to be decreased according to the inhalation amount; and controlling electric power supplied to the heater based on the predicted temperature, such that the temperature of the heater is maintained within a preset range.

13. An aerosol generating apparatus comprising:

a heater configured to generate aerosol;

a sensor configured to sense air introduced into the aerosol generating apparatus according to a puff;

a processor configured to determine a temperature control profile with respect to the heater based on a result of sensing the air introduced into the aerosol generating apparatus, and control electric power supplied to the heater according to the temperature control profile, wherein the temperature control profile corresponds to one section of temperature profile information, the temperature profile information comprising (i) at least one vaporizing temperature retaining section for the heater, in which a vaporizing material is heated to a predetermined temperature or greater to discharge the vaporizing material, (ii) at least one vaporizing temperature decreasing section, in which a temperature of the heater is decreased to a minimum vaporizing temperature due to an absence of a puff, (iii) at least one minimum vaporizing temperature retaining section in which the minimum vaporizing temperature is maintained, and (iv) at least one puff section in which the temperature of the heater is decreased from the minimum vaporizing temperature due to an occurrence of the puff, wherein the temperature control profile corresponds to information, included in the temperature profile information, about a temperature that the heater has to reach within a predetermined time period in a corresponding section, and information about the electric power supplied to the heater in correspondence with the corresponding section.

14. The aerosol generating apparatus of claim 13, wherein the processor selects one temperature control profile corresponding to the result of sensing, from among a plurality of temperature control profiles.

15. The aerosol generating apparatus of claim 13, wherein
the result of sensing comprises an inhalation amount generated per one puff of a user, and
the processor determines a temperature control profile corresponding to the inhalation amount generated per one puff of the user, from among a plurality of temperature control profiles.

16. The aerosol generating apparatus of claim 13, wherein
the sensor senses at least one of an amount of the air introduced into the aerosol generating apparatus according to the puff, a temperature of the air, and velocity of the air, and
the processor selects one temperature control profile from among a plurality of temperature control profiles based on at least one of the amount of the air, the temperature of the air, and the velocity of the air.

* * * * *